US010244771B2

(12) United States Patent
Kouwen et al.

(10) Patent No.: US 10,244,771 B2
(45) Date of Patent: Apr. 2, 2019

(54) **NON-CRISPR-MEDIATED PHAGE RESISTANT *STREPTOCOCCUS THERMOPHILUS***

(71) Applicant: DSM IP ASSETS B.V., Heerlen (NL)

(72) Inventors: Roelof Hendrik Matthijs Kouwen, Echt (NL); Laurens Leendert Hanemaaijer, Echt (NL); Douwe Van Sinderen, Carrigro (IE); Brian McDonnell, Cork (IE); Jennifer Mahony, Blarney (IE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/327,661

(22) PCT Filed: Jul. 23, 2015

(86) PCT No.: PCT/EP2015/066910
§ 371 (c)(1),
(2) Date: Jan. 20, 2017

(87) PCT Pub. No.: WO2016/012552
PCT Pub. Date: Jan. 28, 2016

(65) Prior Publication Data
US 2017/0196233 A1  Jul. 13, 2017

(30) Foreign Application Priority Data

Jul. 24, 2014 (EP) .................................... 14178292

(51) Int. Cl.
| | |
|---|---|
| *A23C 9/123* | (2006.01) |
| *C12N 15/90* | (2006.01) |
| *C12N 15/74* | (2006.01) |
| *C12N 15/113* | (2010.01) |
| *C12N 1/20* | (2006.01) |
| *A23C 19/032* | (2006.01) |
| *C12N 1/36* | (2006.01) |

(52) U.S. Cl.
CPC ........ *A23C 9/1238* (2013.01); *A23C 19/0323* (2013.01); *C12N 1/20* (2013.01); *C12N 1/36* (2013.01); *C12N 15/113* (2013.01); *C12N 15/746* (2013.01); *C12N 15/902* (2013.01); *A23Y 2240/75* (2013.01); *C12N 2310/11* (2013.01)

(58) Field of Classification Search
CPC .............. A23C 9/1238; A23C 19/0323; C12N 15/746; C12N 15/113; C12N 15/902; C12N 2310/11; A23Y 2240/75
See application file for complete search history.

(56) References Cited

PUBLICATIONS

Zhou et al., Cell Mol Life Sci 63(19-20):2260-2290, 2006.*
Kozak, M., Gene 234:187-208, 1999.*
Moineau et al., Applied and Environmental Microbiology 61(7):2461-2466, 1995.*
Klieve et al., FEMS Microbiology Letters 80:155-160, 1991.*
Good et al., Frontiers in Microbiology vol. 2, article 185, pp. 1-11, 2011.*
Nakashima et al., Int. J. Mol. Sci. 15:2773-2793, 2014.*
Marie-Eve Dupuis et al: "CRISPR-Cas and restriction-modification systems are compatible and increase phage resistance", Nature Communications, (Jul. 2, 2013).
Helene Deveau et al: "Phage response to CRISPR-Encoded resistance in *Streptococcus thermophilus*", Journal of Bacteriology, American Society for Microbiology, US vol. 190, No. 4, (Feb. 1, 2008), pp. 1390-1400.
Jennifer Mahony et al: "Progress in lactic acid bacterial phage research", Microbial Cell Factories, Biomed Central, London, NL, vol. 13, No. Suppl 1, (Aug. 29, 2014), p. S1.
David O'Sullivan et al: "Design of a Phage-Insensitive Lactococcal Dairy Starter via Sequential Transfer of Naturally Occurring Conjugative Plasmids", Applied and Environmental Microbiology, vol. 64, No. 11, (Nov. 1, 1998), pp. 4618-4622.
S. Mills et al: "CRISPR analysis of bacteriophage-insensitive mutants (BIMs) of industrial *Streptococcus thermophilus*—implications for starter design", Journal of Applied Microbiology, vol. 108, No. 3, (Mar. 1, 2010), pp. 945-955.
Josephsen J et al: "Stacking of three different restriction and modification systems in Lactococcus lactis by cotransformation", Plasmid, New York,NY, US, vol. 23, No. 1, (Jan. 1, 1990), pp. 71-75.
Larbi, Dejla et al., "Different bacteriophage resistance mechanisms in *Steptococcus salivarius* subsp. *thermophilus*", Journal of Dairy Research, Aug. 1992, pp. 349-357, vol. 59.

* cited by examiner

*Primary Examiner* — Delia M Ramirez
(74) *Attorney, Agent, or Firm* — McBee Moore Woodward & Vanik IP, LLC; Susan McBee; Chester Moore

(57) ABSTRACT

The present invention provides a method for the construction of a bacteriophage-insensitive mutant of a *Streptococcus thermophilus* parent strain whereby the bacteriophage insensitivity is not based on the CRISPR resistance mechanism but based on another mechanism. The method provides a protocol by which this can be achieved by inactivating one or more of the CRISPR systems present in a given strain. The invention also provides the bacteriophage-insensitive mutants as well as their use in a process for making a dairy product.

11 Claims, 8 Drawing Sheets
Specification includes a Sequence Listing.

1 2 3 4 5 6 7 8 9 10 11 12

NON-CRISPR-MEDIATED PHAGE RESISTANT *STREPTOCOCCUS THERMOPHILUS*

CROSS REFERENCE TO RELATED APPLICATIONS

This application is a § 371 National State Application of PCT/EP2015/066910, filed Jul. 23, 2015, which claims priority to European Application No. 14178292.0 filed Jul. 24, 2014.

FIELD OF THE INVENTION

The present invention relates to a method for the construction of bacteriophage-insensitive *Streptococcus thermophilus* mutants, whereby a Clustered Regularly Interspaced Short Palindromic Repeats (CRISPR) system is attenuated, leading to phage resistance being conferred by an alternative mechanism.

DESCRIPTION OF RELATED ART

The thermophilic lactic acid bacterium *Streptococcus thermophilus* is widely used as a starter culture to improve the texture and flavour of many yoghurt and cheese products (Mora et al. (2002) *Genetic diversity and technological properties of Streptococcus thermophilus strains isolated from dairy products.* J Appl Microbiol, 93, 278-287). Consistent predation by (bacterio)phages, however, is still a major cause of economic losses in the dairy industry worldwide—despite a growing genetic and technological knowledge of both the hosts and phages (Goh, Y J et al (2011) *Specialized adaptation of a lactic acid bacterium to the milk environment: the comparative genomics of Streptococcus thermophilus LMD-9.* Microb Cell Fact, 10 Suppl 1, S22). To safeguard against losses of this type, it is necessary to develop robust and diverse Bacteriophage Insensitive Mutants (BIMs) of *S. thermophilus* starters for use in rotation.

Host defences against bacteriophage attack are frequently mediated by the Clustered Regularly Interspaced Short Palindromic Repeats (CRISPR) systems in *S. thermophilus* (Mills, S. et al. (2010). *CRISPR analysis of bacteriophage-insensitive mutants (BIMs) of industrial Streptococcus thermophilus—implications for starter design.* J Appl Microbiol, 108, 945-955), of which there are four known types in this bacterial species (Sinkunas, T et al. (2013). *In vitro reconstitution of Cascade-mediated CRISPR immunity in Streptococcus thermophilus.* EMBO J, 32, 385-394.). It is thought, however, that only CRISPR1 and CRISPR3 are active in *S. thermophilus*, being the only two systems which have been shown to provide acquired immunity against phages (Sinkunas, T. et al., 2013). CRISPR1 and 3 are both classified as 'Type II' systems, based on the structure and composition of the cas gene+repeat-spacer locus. The mechanism by which the CRISPR1 and CRISPR3 systems provide immunity from bacteriophage attack has been well characterised, and follows phage attachment and DNA injection into the host cell.

The non-native DNA triggers the CRISPR-associated (Cas) gene products to target and incorporate a short phage-derived nucleotide segment ("spacer") into the adjacent repeat-spacer locus on the host chromosome, a mechanism which is presumed to be mediated by the cas7 gene (Barrangou, R., et al. (2007). *CRISPR provides acquired resistance against viruses in prokaryotes.* Science, 315, 1709-1712). Subsequently, the system targets and degrades the incoming viral genome through the activity of the CRISPR-associated (Cas) 9 gene product (Sapranauskas, R., et al. (2011). *The Streptococcus thermophilus CRISPR/Cas system provides immunity in Escherichia coli.* Nucleic acids research, 39, 9275-9282). For this reason, cas9 is now described as the 'signature' gene of the Type II CRISPR systems (Makarova, K. S., et al. (2011). *Evolution and classification of the CRISPR-Cas systems. Nature Reviews Microbiology*, 9, 467-477) to which both CRISPR1 and 3 belong.

It is thought that, of the four systems, CRISPR1-mediated resistance is favoured by *S. thermophilus*, due to a higher frequency of spacer incorporation in this locus in some strains (Deveau, H., et al. (2008)). *Phage response to CRISPR-encoded resistance in Streptococcus thermophilus. Journal of bacteriology*, 190, 1390-1400; Mills et al (2010. Despite the effectiveness of the CRISPR1 system in providing acquired immunity to *S. thermophilus* against attacking phages, reliance on this natural mechanism in an industrial setting is not favourable. Deveau et al. (2008) showed that in order to evade the CRISPR1 system, the attacking phage merely needs to possess a single nucleotide polymorphism (SNP) in the segment from which the initial spacer was derived—highlighting the frequent instability of the system. The need for an alternative, more stable mechanism of phage-resistance (and a method to select for it) is evident. For these reasons, two of the cas genes (cas7 and cas9) forming part of the CRISPR1-Cas system, were selected for targeted inactivation in this study.

The method of employing antisense RNA (previously referred to as micRNA) plasmid constructs to inhibit the expression of specific genes in bacteria and bacteriophages has been well established (Coleman, J. et al. (1985). *A novel immune system against bacteriophage infection using complementary RNA (micRNA).* Nature, 315, 601-603; Kim & Batt, (1991). *Antisense mRNA-Mediated Bacteriophage Resistance in Lactococcus lactis subsp. lactis.* Appl Environ Microbiol, 57, 1109-1113. The *L. lactis* high copy plasmid pNZ44 was devised by McGrath, S. et al (2001) (*Improvement and optimization of two engineered phage resistance mechanisms in Lactococcus lactis.* Appl Environ Microbiol, 67, 608-616) to optimize an antisense strategy to silence phage genes involved in DNA replication, thereby increasing the phage resistance of the host. However, to our knowledge, the system has not been used to inactivate CRISPR-Cas genes prior to bacteriophage infection. The present invention provides a method to bias the generation of spontaneous BIMs in a manner which favours a CRISPR-independent mechanism of resistance. The invention also details a method whereby a phage-resistant mutant containing both CRISPR and non-CRISPR elements may be selected for.

DETAILED DESCRIPTION OF A PREFERRED EMBODIMENT

Figure 1:
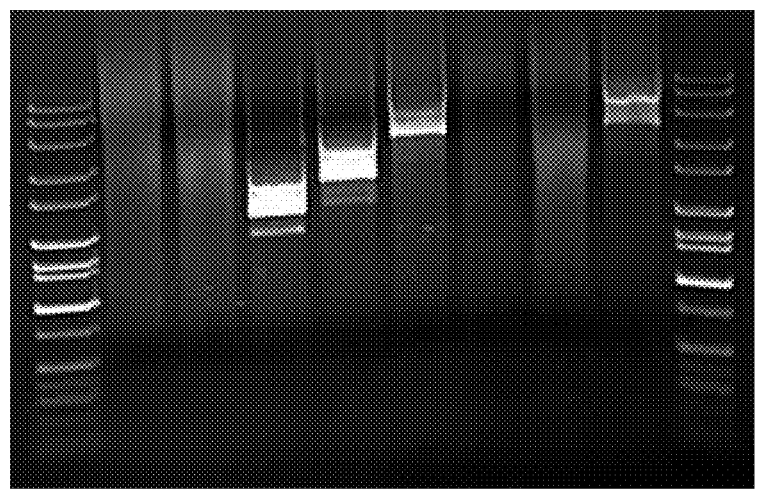
FIGS. 1-13 depict embodiments as described herein.

In a first aspect, the invention provides a method for the construction of a bacteriophage insensitive mutant of a Streptococcus thermophilus parent strain comprising the steps of
  a. inactivating the CRISPR resistance mechanism of the parent strain;

b. exposing the parent strain obtained in step a) to a bacteriophage;
c. isolating bacteriophage insensitive mutants;
d. optionally: comparing the CRISPR loci of the parent strain with the CRISPR loci of the bacteriophage insensitive mutants; and
e. optionally: selecting bacteriophage insensitive mutants of which the CRISPR loci is identical to the CRISPR loci of the parent strain.

The bacteriophage insensitive mutant shall be referred to in the remainder of the text as BIM.

The advantage of the method of the invention is that the BIM's have acquired their phage resistance due to a mechanism different from the CRISPR resistance mechanism. In order to avoid that in step b) of the method, CRISPR BIM's are generated, the CRISPR resistance mechanism must be inactivated in step a).

Step a)—According to a preferred embodiment of the method of the invention, the CRISPR resistance mechanism is inactivated by introducing into the parent strain one or more DNA constructs comprising a promoter followed by one or more cas genes or a part thereof or a nucleotide sequence at least 90% identical to the cas gene in the reverse orientation such that the cas gene is transcribed into the corresponding antisense RNA which subsequently binds to the target cas mRNA thereby silencing the cas gene.

The promoter may be any suitable promoter such as pNZ44, derived from *Lactococcus lactis* (McGrath et al., 2001).

Suitable cas genes that may be used are cas genes associated with any functional CRISPR system may be used, provided that the function it performs is essential to the incorporation of additional spacers and/or the successful execution of acquired immunity against attacking phages. Preferred embodiments are cas7 and cas9, associated with the CRISPR1 system in *S. thermophilus* or cas5/csn1, cas1 or csn2 associated with CRISPR3. In the method of the invention a nucleotide sequence may be used that comprises only a part of the cas gene, for instance at least 100 base pairs, or at least 200 base pairs, or at least 300 base pairs. The advantage of this method is to increase the efficiency with which the antisense plasmids are constructed by using a shorter insert. However, preferably the full length cas gene is used for maximum efficiency of gene silencing after transcription to mRNA. Furthermore, in the method of the invention a nucleotide sequence may be used that is at least 90% identical, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% and most preferably 100% identical to the nucleotide sequence the cas gene or the part thereof that is used.

In a preferred embodiment, the CRISPR resistance mechanism is inactivated by introducing into the parent strain one or more DNA constructs comprising a promoter followed by two or more cas genes or a part thereof.

Two or more DNA-constructs may also be used in step a) whereby each DNA-construct may comprise the same or a different cas gene. This method may provide a significant advantage by inactivating two or more functional CRISPR-Cas systems simultaneously, in order to rule out potential transference of activity from an inactivated CRISPR1 system to CRISPR3 or 4, which is equally undesirable for the reasons stated above.

According to a another preferred embodiment of the method of the invention, the CRISPR resistance mechanism is inactivated by introducing into the parent strain one or more DNA constructs comprising a catalytically inactive Cas9 protein and one or more single guide RNAs (sgRNAs) for transcriptional repression of the one or more cas gene(s) in the *Streptococcus thermophilus* parent strain. The gene encoding the catalytically inactive Cas9 protein and a customizable single guide RNA (sgRNA) are co-expressed and the Cas9-sgRNA complex may bind to DNA elements complementary to the sgRNA and may cause a steric block that halts transcript elongation by RNA polymerase, resulting in the repression of the cas9 gene. This method has been shown to be capable of repressing target genes in for instance *Escherichia coli* (Qi. S. et al. (2013) *Repurposing CRISPR as an RNA-guided platform for sequence-specific control of gene expression* Cell. February 28; 152(5):1173-83). This system, which is called CRISPR interference (CRISPRi) by Qi L. S. et al., can efficiently repress expression of targeted genes in *Escherichia coli*, with no detectable off-target effects. CRISPRi can be used to repress multiple target genes simultaneously, and its effects are reversible.

Step b)—Exposing the parent strain obtained in step a) to a bacteriophage may be carried out in any suitable medium, for instance in an aqueous solution such as a buffered aqueous solution or in a soft agar medium or in milk. In a preferred embodiment, exposing the parent strain to a bacteriophage is carried out in a soft agar medium. In another preferred embodiment, exposing the parent strain to a bacteriophage is carried out in milk. The milk may be incubated overnight or until clotting is observed. The parent strain used in the method of the invention may be pre-treated in order to increase the genetic diversity and to increase the number of the BIMs. This pre-treatment may be carried out by methods known in the art, such as chemical mutagenesis or by irradiation with UV-light. The—optionally pre-treated—parent strain may be exposed to one type of bacteriophage or to multiple different bacteriophages, for instance to 2, 3, 4 or 5 different type of bacteriophages.

Step (c)—The suspension or the incubated (clotted) milk obtained in step (a) of the method of the invention may be plated on agar plates. After incubating the agar plates at a temperature at which *Streptococcus thermophilus* may grow, colonies may appear which represent the BIMs. The colonies may be purified to obtain a single strain BIM according to methods known in the art.

Step (d)—In step (d) of the method of the invention, the CRISPR loci of the BIMs obtained in step (c) of the method of the invention are analyzed for their length (in base pairs) and/or sequenced and compared with the CRISPR loci of the bacteriophage sensitive parent strain.

Step (e)—In step (e) of the method of the invention only those BIMs are selected of which the CRISPR loci are identical to the CRISPR loci of the parent strain. The advantage of the method of the invention is, that the selected BIMs have acquired a phage resistance mechanism that is different from CRISPR and therefore based on an alternative phage resistance mechanism. As a result, the BIMs obtained by the method of the invention have a more stable phage resistance compared to a CRISPR BIM of which it is known that phages can rapidly evolve to overcome these spacer additions through single nucleotide alterations in the appropriate genomic region.

In another embodiment of the method of the invention, the one or more DNA constructs that were introduced in step a) of the method of the invention may be removed after step e)

The advantage of this step is that the CRISPR defence mechanism is once again active against the bacteriophages.

The *Streptococcus thermophilus* parent strain used in the method of the invention, may be either be sensitive or be insensitive to the bacteriophage, such as insensitive due to the previous addition of a CRISPR spacer. In the case of a sensitive parent strain, inactivation of the CRISPR defence mechanism prevents the formation of CRISPR BIMs in step b) of the method of the invention. In the case of the insensitive parent strain (such as due to the previous addition of a CRISPR spacer), the parent strain is first made sensitive by inactivation of the CRISPR defence mechanism which then also prevents the formation of phages that have overcome the CRISPR-mediated defence mechanism in step b) of the method of the invention. This may lead to a BIM which is resistant to one or more phages by both CRISPR and non-CRISPR mechanisms.

In a second aspect, the invention provides a bacteriophage-insensitive mutant of a *Streptococcus thermophilus* parent strain wherein the CRISPR loci of the bacteriophage insensitive mutant are identical to the CRISPR loci of the parent *Streptococcus thermophilus* strain and which are obtainable by the method of the first aspect of the invention.

Alternatively, the present invention relates to a bacteriophage-insensitive mutant of a *Streptococcus thermophilus* parent strain wherein the CRISPR loci of the bacteriophage-insensitive mutant are not identical to the CRISPR loci of the parent *Streptococcus thermophilus* strain and which bacteriophage-insensitive mutant further comprises a non CRISR mediated bacteriophage resistance mechanism. Preferably, the non CRISPR mediated bacteriophage resistance mechanism is not a restriction-modification system. Preferably, the non CRISPR mediated bacteriophage resistance mechanism is a resistance mechanism derived from *Streptococcus thermophilus*, or preferably derived from the *Streptococcus thermophilus* parent strain. The advantage of using both a CRISPR and a non CRISPR resistance mechanisms in a BIM is an improved phage resistance. So called 'double hurdle' BIMs have a broader phage resistance, i.e. a defence against several different bacteriophages. Furthermore, double hurdle BIMs have an increased phage robustness, showing resistance for several rounds of exposure to a bacteriophage.

In a preferred embodiment, the present bacteriophage insensitive mutant has an increased sedimentation rate (or an increased pellet weight) and/or an increased chain formation compared to the *Streptococcus thermophilus* parent strain. Preferably, the present bacteriophage insensitive mutant has a pellet weight increase of least 10% of the pellet weight of the parent strain, more preferably at least 20%, more preferably at least 50%, more preferably at least 100%, preferably at least 150%, more preferably at least 200%, more preferably at least 250%, even more preferably at least 300% and most preferably at least 350% of the pellet weight of the parent strain. Preferably, the present bacteriophage insensitive mutant has a percentage increase of average chain length or average cells per chain (CPC) of at least 50%, more preferably at least 100%, preferably at least 150%, more preferably at least 200%, more preferably at least 250%, even more preferably at least 300% and most preferably at least 350% of the averaged CPC of the parent strain.

In a third aspect, the invention provides a process for the production of a dairy product such as a fermented milk product or cheese comprising the use of one or more of the bacteriophage insensitive mutant of a bacteriophage-sensitive *Streptococcus thermophilus* parent strain as disclosed hereinbefore.

In a fourth aspect, the invention provides the use of the bacteriophage-insensitive mutant derived from a bacteriophage-sensitive *Streptococcus thermophilus* parent strain as disclosed hereinbefore in a process for the production of a dairy product, such as a fermented milk or cheese.

Figure Legends

FIG. 1—Plasmid preparations of *S. thermophilus* strain 100-E and derivatives. Lanes 1, 10: 1 kb Full Scale DNA Ladder (Fisher Scientific, U.S.A.), L2: 100-E parent, L3: BIM100-E-D1A-L7, L4: BIM100-E-D1A-L7::pNZ44, L5: BIM100-E-D1A-L7::pNZ44+100-ECas7i, L6: BIM100-E-D1A-L7::pNZ44+100-ECas9i, L7: BIM100-E-D1A-L7::pNZ44+100-ECas9i (cured), L8: BIM100-E-D1A-L5, L9: BIM100-E-D1A-L5::pNZ44+100-ECas9i.

Figure 2:
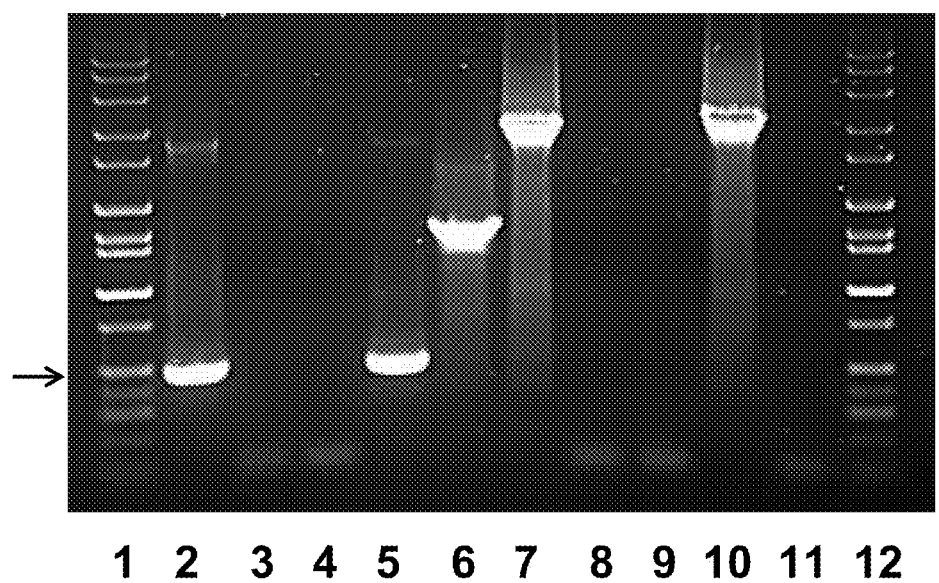

FIG. 2—PCR amplification of pNZ44 MCS regions. Lanes 1, 12: 1 kb Full Scale DNA Ladder, L2: pNZ44 plasmid DNA (+ve control; indicated by arrow), L3: 100-E parent, L4: BIM100-E-D1A-L7, L5: BIM100-E-D1A-L7::pNZ44, L6: BIM100-E-D1A-L7::pNZ44+100-ECas7i, L7: BIM100-E-D1A-L7::pNZ44+100-ECas9i, L8: BIM100-E-D1A-L7::pNZ44+100-ECas9i (cured), L9: BIM100-E-D1A-L5, L10: BIM100-E-D1A-L5::pNZ44+100-ECas9i, L11: Negative control.

Figure 3:
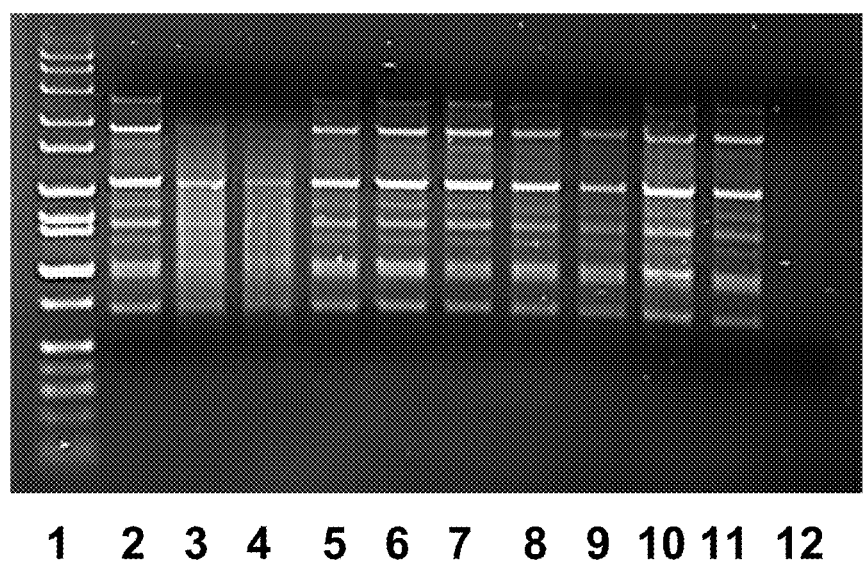

FIG. 3—GTG RAPD fingerprinting of *S. thermophilus* parent strains, BIMs and transformants used in this study. Lane 1: 1 kb Full Scale DNA Ladder (, L2: 100-E parent, L3: 100-E::pNZ44+100-ECas7i, L4: 100-E::pNZ44+100-ECas9i, L5: BIM100-E-D1A-L7, L6: BIM100-E-D1A-L7::pNZ44, L7: BIM100-E-D1A-L7::pNZ44+100-ECas7i, L8: BIM100-E-D1A-L7::pNZ44+100-ECas9i, L9: BIM100-E-D1A-L7::pNZ44+100-ECas9i (cured), L10: BIM100-E-D1A-L5, L11: BIM100-E-D1A-L5::pNZ44+100-ECas9i, L12: Negative control.

Figure 4:
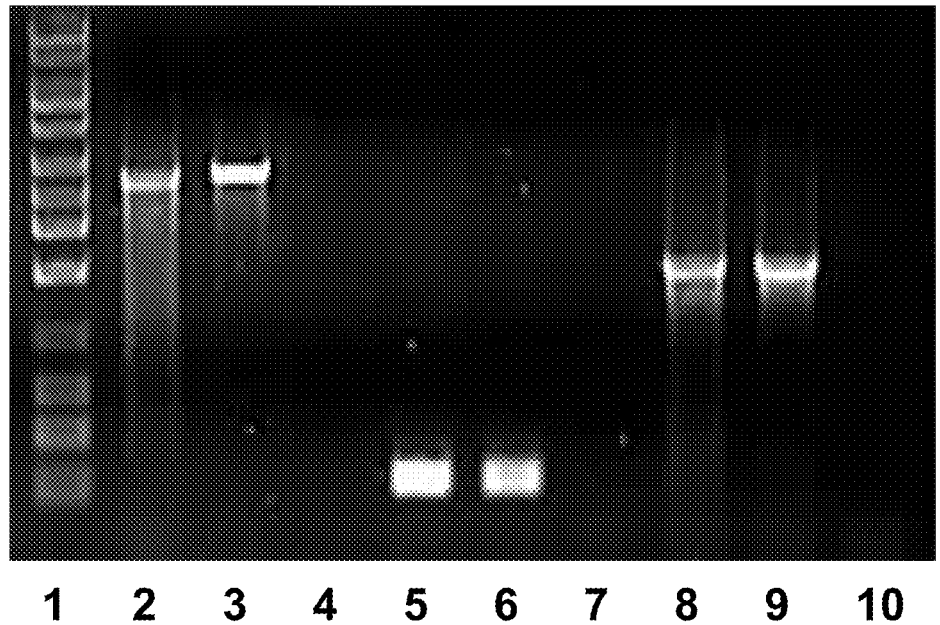

FIG. 4—PCR amplification of CRISPR (C1, C2, C3) loci of *S. thermophilus* strain 100-E and its derivatives. Lane1: 1 kb Full Scale DNA Ladder, L2: 100-E parent C1, L3: BIM100-E-D1A-L7::pNZ44+100-ECas9i C1, Lanes 4, 7 & 10: -ve controls, L5: 100-E parent C2, L6: BIM100-E-D1A-L7::pNZ44+100-ECas9i C2, L8: 100-E parent C3, L9: BIM100-E-D1A-L7::pNZ44+100-ECas9i C3.

Figure 5:
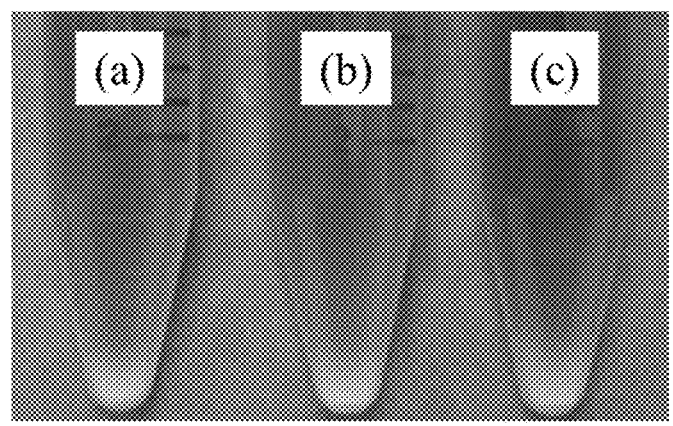

FIG. 5—Observed sedimentation of S. thermophilus strain 100-E parent (a) and its derived BIMs. (b) BIM100-E-D1A-L-7 (CRISPR BIM), (c) BIM100-E-D1A-L-5 (non-CRISPR BIM).

Figure 6:
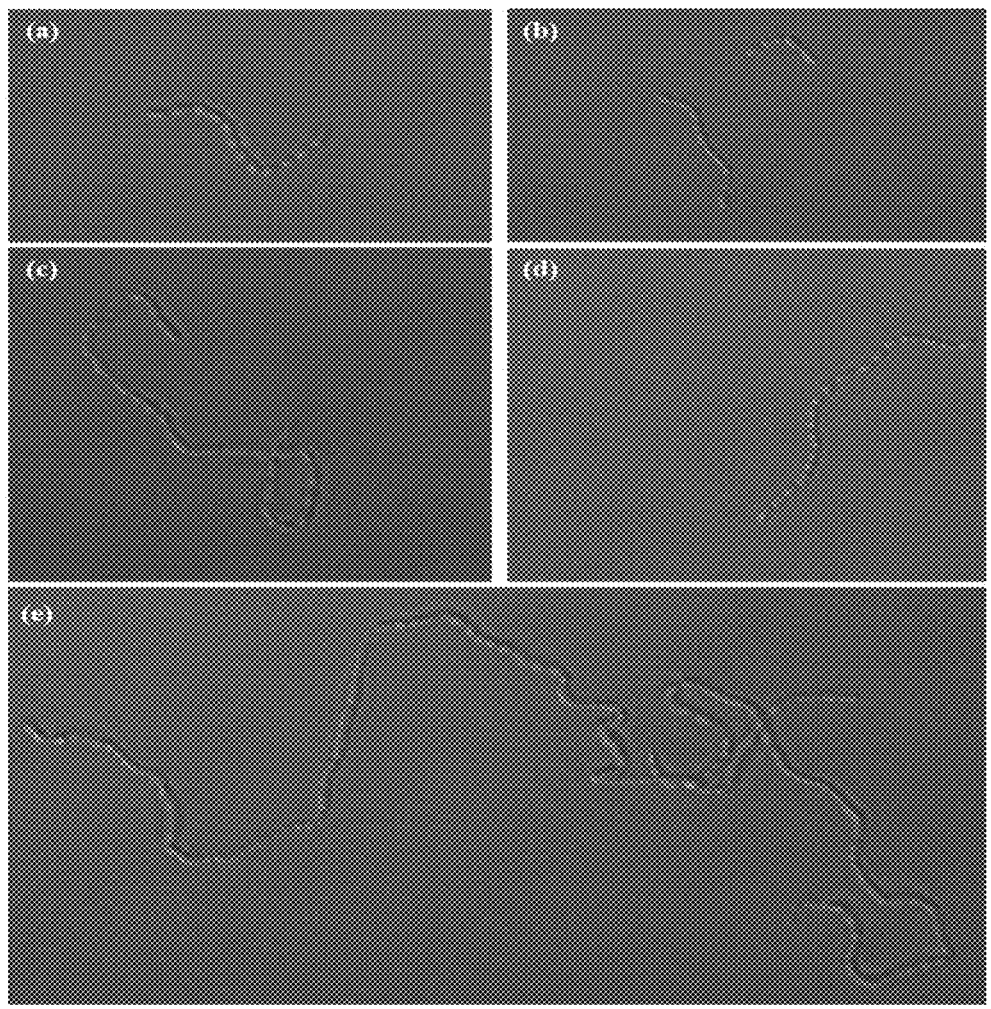

FIG. 6—Representative images of *S. thermophilus* 100-E (and derived BIMs) cell chains visualised using a confocal laser scanning microscopy. (a) 100-E WT, (b) BIM100-E-D1A-L7, (c) BIM100-E-D1A-L5, (d) BIM100-E-DH51, (e) BIM100-E-DH61.

Figure 7:
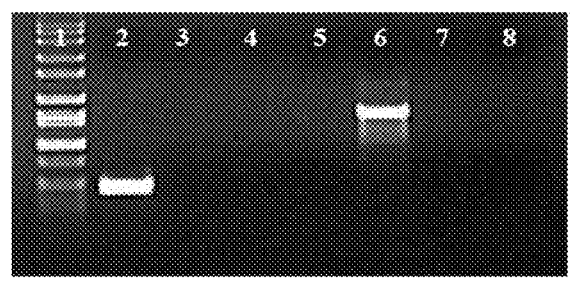

FIG. 7—PCR amplification of pNZ44 MCS regions. Lane 1: 1 kb Full Scale DNA Ladder, L2: pNZ44 plasmid DNA (positive control), L3: negative control, L4: 100-E WT, L5: BIM100-E-D1A-L7, L6: BIM100-E-D1A-L7::pNZ44+100-ECas7i, L7: BIM100-E-DH51, L8: BIM100-E-DH61.

Figure 8:
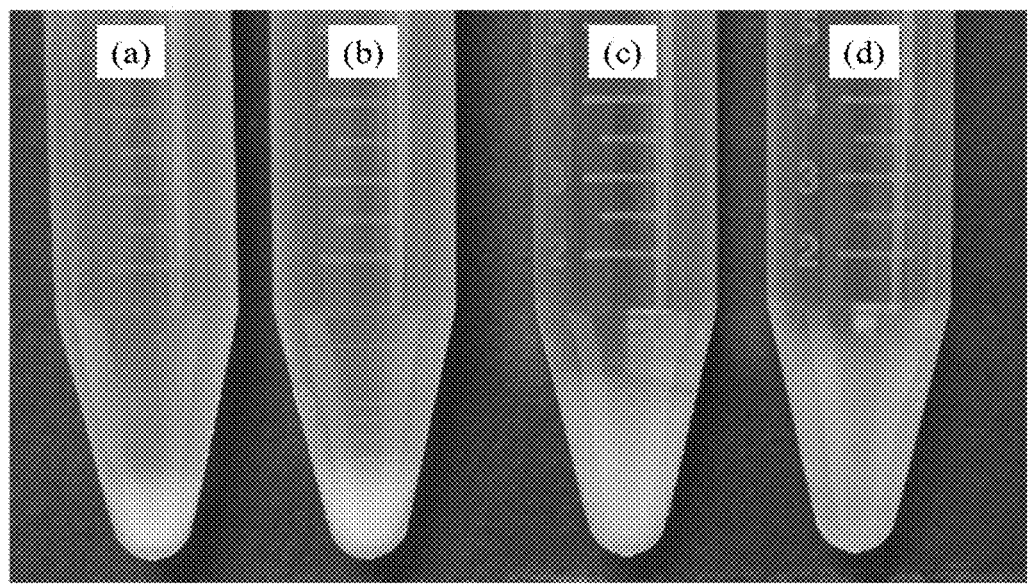

FIG. 8—Observed sedimentation profile of *S. thermophilus* 100-E and derived BIMs. (a) 100-E WT, (b) BIM100-E-D1A-L7, (c) BIM100-E-DH51, (d) BIM100-E-DH61.

Figure 9:
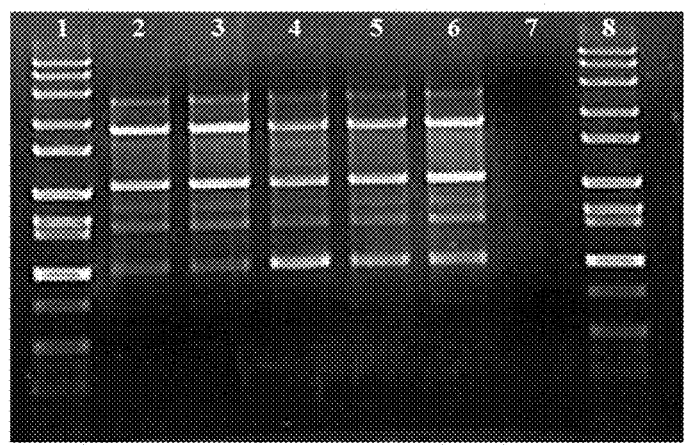

FIG. 9—GTG RAPD fingerprinting of *S. thermophilus* 100-E parent strain and derived BIMs. Lane 1; 8: 1 kb Full Scale DNA Ladder, L2: 100-E WT, L3: BIM100-E-D1A-L5, L4: BIM100-E-D1A-L7, L5: BIM100-E-DH51, L6: BIM100-E-DH61, L7: negative control.

Figure 10:
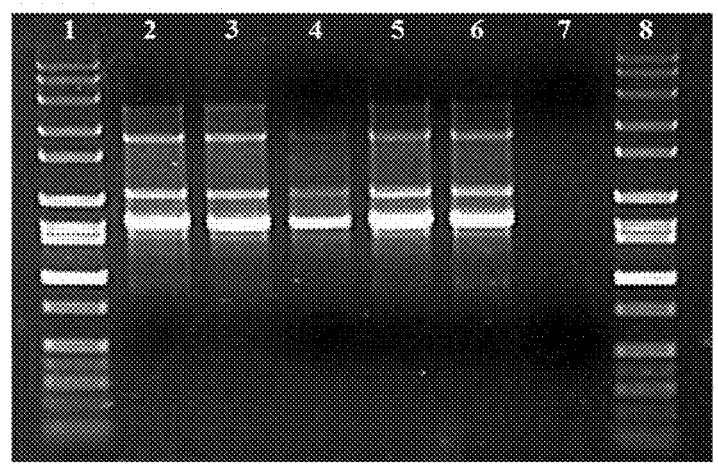

FIG. 10—GTG RAPD fingerprinting of *S. thermophilus* 100-F parent strain and transformants. Lane 1: 1 kb Full Scale DNA Ladder, L2: 100-F WT, L3: BIM100-F-

NGBD1A-L2, L4: BIM100-F-NGBD1A-L2::pNZ44, L5: BIM100-F-NGBD1A-L2::pNZ44+100-FCas9i, L6: BIM100-F-NGBD1A-L2::pNZ44+100-FCas9i (cured), L7: negative control.

Figure 11:
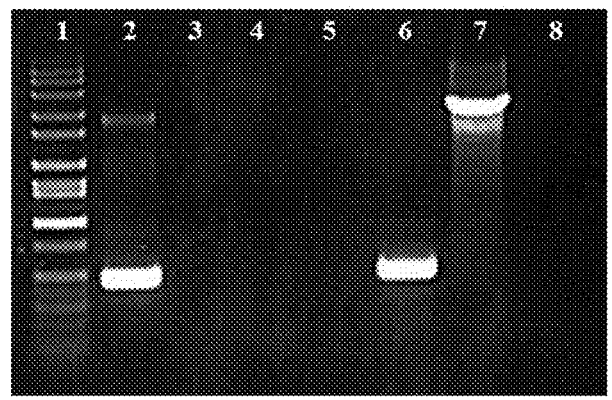

FIG. 11—PCR amplification of pNZ44 MCS regions. Lanes 1: 1 kb Full Scale DNA Ladder, L2: pNZ44 plasmid DNA (positive control), L3: negative control, L4:100-F WT, L5: BIM100-F-NGBD1A-L2, L6: BIM100-F-NGBD1A-L2::pNZ44, L7: BIM100-F-NGBD1A-L2::pNZ44+100-FCas9i, L8: BIM100-F-NGBD1A-L2::pNZ44+100-FCas9i (cured).

Figure 12:
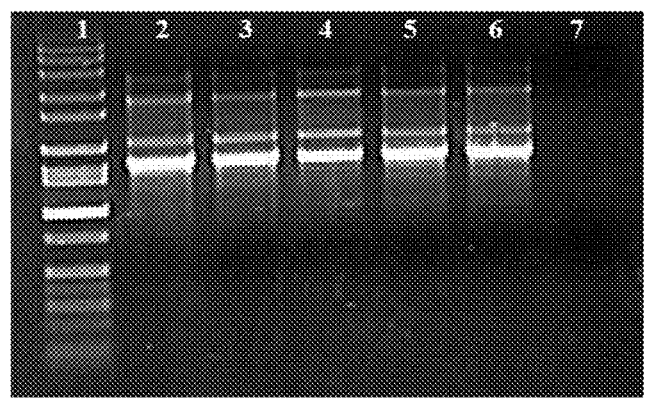

FIG. 12—GTG RAPD fingerprinting of *S. thermophilus* 100-F parent strain and transformants. Lane 1; 8: 1 kb Full Scale DNA Ladder, L2: 100-F WT, L3: 100-FWT::pNZ44 (plasmid control), L4: 100-F::pNZ44+100-FCas7i, L5: 100-F::pNZ44+100-F2Casi, L6: 100-F::pNZ44+100-F2CasSWi, L7: negative control.

Figure 13:
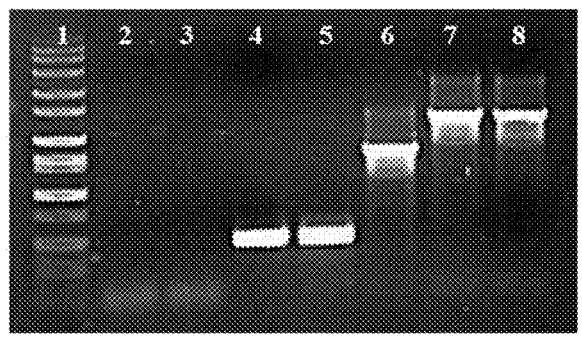

FIG. 13—PCR amplification of pNZ44 MCS regions. Lane 1: 1 kb Full Scale DNA Ladder, L2: 100-F WT, L3: negative control, L4: pNZ44 plasmid DNA (positiveve control), L5: 100-FWT::pNZ44 (plasmid control), L6: 100-F::pNZ44+100-FCas7i, L7: 100-F::pNZ44+100-F2Casi, L8: 100-F::pNZ44+100-F2CasSWi.

Materials And Methods

1. Bacterial Growth Conditions

Individual strains of *S. thermophilus* were routinely grown from 20% Reconstituted Skimmed Milk (RSM) stocks, 20% glycerol stocks (Sigma Aldrich, Germany) or from a single colony overnight (ON) at 42° C. in M17 Broth (Oxoid, U.K.) supplemented with 0.5% lactose (LM17) or on plates containing 10 g/L technical agar (Merck, Germany). In phage enumeration assays, as adapted from Lillehaug, D. ((1997) *An improved plaque assay for poor plaque-producing temperate lactococcal bacteriophages.* J Appl Microbiol, 83, 85-90). LM17 broth was supplemented with 0.25% glycine (Oxoid, U.K.), 10 mM CaCl$_2$ (Oxoid, U.K.) and either 10 g/L (solid agar base) or 4 g/L (semi-solid overlay) technical agar. The semi-solid agar was sterilised by autoclaving at 121° C. for 15 minutes or by boiling for 7 minutes in a microwave whereas the solid agar was boiled for 7 minutes in a microwave. *L. lactis* NZ9000 was maintained as above with the following modifications: overnight (ON) cultures were grown at 30° C. with the substitution of glucose (Sigma-Aldrich, Germany) in place of lactose. All transformants were maintained as above with the addition of chloramphenicol (Sigma-Aldrich, Germany) to a final concentration of 5 µg/ml (L/GM17+Cm5).

2. Isolation and Selection of Bacteriophages

Whey samples from dairy plants producing fermented milk products were obtained and analysed for the presence of phages against *S. thermophilus* 100-E using the spot assay described below under "Bacteriophage assays". Defined single plaques were isolated by twice single plaque purification on semi-solid overlays. Phages were then propagated as follows: 10 ml LM17 broth was inoculated (1%) with a fresh ON culture of the appropriate host strain and incubated at 42° C. for 1.0-2.5 hours. Then, a single plaque was added to the growing culture, mixed well and incubated for a further 2-4 hours. The lysed culture was centrifuged and the supernatant filtered (0.45 µm). The filtered supernatant was used as the phage stock for subsequent assays. Table 1 summarizes the phages that were obtained in this manner.

TABLE 1

A list of strains and phages used in this study

| | Description | Source |
|---|---|---|
| Strain | | |
| *Streptococcus thermophilus* 100-E | Parent strain | DSM, The Netherlands |
| *L. lactis* NZ9000 | Transformation vector | a) |
| BIM100-E-D1A-L7 | CRISPR-mediated BIM | UCC, Cork, Ireland |
| BIM100-E-D1A-L5 | Non-CRISPR BIM | " |
| BIM100-E-DH51 | Double Hurdle BIM | " |
| BIM100-E-DH61 | Double Hurdle BIM | " |
| *Streptococcus thermophilus* 100-F | Parent strain | DSM, The Netherlands |
| BIM100-F-NGBD1A-L2 | CRISPR-mediated BIM | UCC, Cork, Ireland |
| Phage | | |
| φ100-E-D1A-L | Virulent phage of *S. thermophilus* 100-E | DSM, The Netherlands |
| φ100-E-D2A-L | " | " |
| φ100-E-D3A-L | " | " |
| φ100-E-D4A-L | " | " |
| φSTV84-D1A-L | Virulent phage of *S. thermophilus* 100-F | " |
| φSTV88-D1A-L | " | " |
| φNGB-D1A-L | " | " | a) Fernandez, L., et al (2000). *Cloning, characterization, controlled overexpression, and inactivation of the major tributyrin esterase gene of Lactococcus lactis.* Appl Environ Microbiol, 66, 1360-1368.

*Streptococcus thermophilus* 100-E=DS64900 was deposited on 15 Jul. 2014 with the Centraal Bureau for Schimmelcultures, Uppsalalaan 8, 3508 AD in Utrecht, The Netherlands and received deposition number CBS138555.

*Streptococcus thermophilus* 100-F=DS64985 was deposited on 6 May 2015 with the Centraal Bureau for Schimmelcultures, Uppsalalaan 8, 3508 AD in Utrecht, The Netherlands and received deposition number CBS139996.

3. BIMs of *S. thermophilus* 100-E and 100-F

BIMs against phage φ100-E-D1A-L were generated by adding 500 µl fresh ON culture of *S. thermophilus* 100-E and 10 to 100 µl undiluted phage lysate as indicated (phages isolated from a single plaque, titre approx. 1×10$^7$ pfu/ml) to 4 ml soft LM17 agar, followed by spreading this suspension on solid agar. In the case of 100-F and where insufficient BIMs were isolated using ON incubation, the amount of culture added was increased to 1000 µl and the amount of phage lysate to 100 µl. Colonies, representing potential BIMs, growing in the top layer were twice single colony-purified and subjected to phage assays and CRISPR sequencing as described below. For 100-E, two BIMs were thus obtained and selected for characterization (see below): *S. thermophilus* BIM100-E-D1A-L5 and BIM100-E-D1A-L7. A further two BIMs, derived from BIM100-E-D1A-L7, were also generated in this manner (BIM100-E-DH51 and BIM100-E-DH61; Table 1). All 100-F BIMs (Table 1) were generated in this manner, with the modifications indicated above. Where insufficient numbers of BIMs were generated using this method, the procedure was repeated using the appropriate WT or transformed strain until an acceptable number of BIMs was isolated.

4. Bacteriophage Assays

Spot assays were performed by seeding the LM17 semi-solid agar overlay with 500 µl fresh ON culture and applying 10 µl of phage lysate in a grid format, as described by Dupont, K., et al, J. (2005) (*Detection of lactococcal 936-species bacteriophages in whey by magnetic capture hybridization PCR targeting a variable region of receptor-binding*

*protein genes.* J Appl Microbiol, 98, 1001-1009). Plates were then allowed to dry and incubated anaerobically ON at 42° C. A clear zone was assumed to indicate phage-mediated lysis of the bacterial lawn by the applied phage and was recorded as '+', whereas absence of lysis was recorded as '−'.

For phage enumeration, plaque assays were performed by adding 500 µl culture and 10 µl of neat or appropriately diluted phage lysate to 4 ml semi-solid agar, followed by plating on LM17 agar plates as described above with subsequent ON incubation at 42° C. Efficiency of plaquing (EOP) was calculated by dividing the obtained titre of a given phage on the test strain by the titre of the same phage on the parent strain.

5. PCR Screening & CRISPR Locus Sequencing

All BIMs generated were subjected to PCR profiling to confirm their relatedness to the relevant parent strain from which they were derived, either by RAPD PCR or by CRISPR locus sequencing. RAPD PCR was performed on single colonies of each parent strain and BIM as template for the reaction and using the '(GTG)5' RAPD profiling primer (Gevers, D., et al. (2001). *Applicability of rep-PCR fingerprinting for identification of Lactobacillus species.* FEMS Microbiol Lett, 205, 31-36). The PCR conditions were as follows: 95° C.×10 min, followed by 30 cycles of 95° C.×15 s, 40° C.×30 s and 72° C. for 8 min with a final extension step of 72° C. for 16 min.

BIMs generated were purified and the CRISPR loci amplified by PCR and sequenced to determine acquisitions or alterations to the spacer content of the BIMs. CRISPR-1, CRISPR-2 and CRISPR-3 repeat/spacer arrays for each strain were amplified individually using a single colony of the appropriate strain as template material for the PCR and primers described previously by Horvath, P et al. (2008). *Diversity, activity and evolution of CRISPR loci in Streptococcus thermophilus.* Journal of bacteriology, 190, 1401-1412). Primers targeting the CRISPR4 locus of 100-F were designed specifically for this strain, as no homolog of CRISPR4 is present in 100-E. The PCR conditions were as follows: 95° C.×10 min, followed by 30 cycles of 95° C.×15 s, 55° C.×15 s and 72° C. for either 2 min 45 s (CRISPR-1) or 1 min 10 s (CRISPR-2, CRISPR-3 and CRISPR-4) with a final extension step of 72° C. for 10 min.

The PCR generated products were visualised on a 1% agarose (Fisher Scientific, USA) gel and purified using a PCR purification spin kit (Genomed, Germany). Sanger sequencing (of all PCR products and plasmids) was performed by MWG Biotech to verify the integrity of all plasmid constructs and to compare the sequences of the CRISPR loci of the BIMs to those of the corresponding parent strain (Eurofins, Germany). For CRISPR loci, this was performed by primer walking using synthetic primers based on a unique spacer of each repeat/spacer array in the internal regions of the sequences of the CRISPR loci, where required. CRISPRs were assembled using the Seqman program (DNAstar) and CRISPR arrays were visualised using the online CRISPR finder program from the Universite of Paris sud-11.

TABLE 2

PCR primers used in this study

| SEQ. ID. No | Primer name | Sequence (5' → 3') | Ref | Target |
|---|---|---|---|---|
| 1 | yc70 | TGCTGAGACAACCTAGTCTCTC | a) | CRISPR1 |
| 2 | CR1-rev | TAAACAGAGCCTCCCTATCC | a) | CRISPR1 |
| 3 | CR1-gfwd | CCTGTCATCTCTGGGAGT | b) | CRISPR1 |
| 4 | CR1-g2fwd | CGGTGTTCTATATCGAGGTC | b) | CRISPR1 |
| 5 | CR1-grev | GGAGACACAGGAGTAGGAAAG | b) | CRISPR1 |
| 6 | CR1-g2rev | GGAGACACAGGAGTAGGAAAG | b) | CRISPR1 |
| 7 | CR2-fwd | TTAGCCCCTACCATAGTGCTG | a) | CRISPR2 |
| 8 | CR2-rev | TTAGTCTAACACTTTCTGGAAGC | a) | CRISPR2 |
| 9 | CR3-fwd | CTGAGATTAATAGTGCGATTACG | a) | CRISPR3 |
| 10 | CR3-rev | GCTGGATATTCGTATAACATGTC | a) | CRISPR3 |
| 11 | (GTG)5 | GTGGTGGTGGTGGTG | | Strain specific fingerprint |
| 12 | 100-ECas7PstIF | AGCAGCCTGCAGGCAAGAGGAAATCGTCAGTG | b) | 100-E cas7 |
| 13 | 100-ECas7NcoIR | AGCAGCCCATGGTCAATCCTTACTTTCTAA | b) | 100-E cas7 |
| 14 | 100-ECas9XbaIF | AGCAGCTCTAGAGTCGTTAGAGGGAGGATTAC | b) | 100-E cas9 |
| 15 | 100-ECas9PstIR | AGCAGCCTGCAGTTAAAAATCTAGCTTAGGC | b) | 100-E cas9 |
| 16 | pNZ44fwd | CTAATGTCACTAACCTGCCCC | b) | pNZ44 |
| 17 | pNZ44rev | GCTTTATCAACTGCTGCT | b) | pNZ44 |
| 18 | CR4-fwd | GATTCAGTTCCTCATAGAGC | b) | CRISPR4 |
| 19 | CR4-rev | GACCTCAACCAATCGATTG | b) | CRISPR4 |

TABLE 2-continued

PCR primers used in this study

| SEQ. ID. No | Primer name | Sequence (5' → 3') | Ref | Target |
|---|---|---|---|---|
| 20 | 100-FCas7XbaIF | AGCAGCTCTAGACAGTGATAATAAGTTGGTGGT | b) | 100-F cas7 |
| 21 | 100-FCas7PstIR | AGCAGCCTGCAGCTGTCCTTGTCAATCCTTAC | b) | 100-F cas7 |
| 22 | 100-FCsn2PstIF | AGCAGCCTGCAGGCCAATTCAGAGGAAAGG | b) | 100-F csn2 |
| 23 | 100-FCsn2NcoIR | AGCAGCCCATGGCAAGATGTGACTGTCACC | b) | 100-F csn2 |
| 24 | 100-FCsn2XbaIFSW | AGCAGCTCTAGAGCCAATTCAGAGGAAAGG | b) | 100-F csn2 |
| 25 | 100-FCsn2PstIRSW | AGCAGCCTGCAGCAAGATGTGACTGTCACC | b) | 100-F csn2 |
| 26 | 100-FCas7PstIFSW | AGCAGCCTGCAGCAGTGATAATAAGTTGGTGGT | b) | 100-F cas7 |
| 27 | 100-FCas7NcoIRSW | AGCAGCCCATGGCTGTCCTTGTCAATCCTTAC | b) | 100-F cas7 |
| 28 | 100-FC as9XbaIF | AGCAGCTCTAGAGTTGCGAATTTTCAGATAC | b) | 100-F cas9 |
| 29 | 100-FCas9PstIR | AGCAGCCTGCAGGTAACTGTGTAAGGCGCC | b) | 100-F cas9 | a) Horvath, et al., 2008
b) This study

6. Preparation of Competent Cells

Competent cells were prepared as described by Holo & Nes ((1989). *High-Frequency Transformation, by Electroporation, of Lactococcus lactis subsp. cremoris Grown with Glycine in Osmotically Stabilized Media*. Appl Environ Microbiol, 55, 3119-3123), with the following modifications: A series of tubes containing 10 ml LM17 or GM17 (for *L. lactis*) broth and varying (from 0.2% to 2.4%) concentrations of either glycine (Sigma-Aldrich, Germany) or threonine (Sigma-Aldrich, Germany) were prepared and inoculated (1%) with a fresh ON culture. The tubes were incubated at 42° C. ON and examined for growth. LM17 broth containing 0.5% sucrose (Sigma-Aldrich, Germany; SLM17) supplemented with the highest level of glycine or threonine tolerated by the strains was used to prepare competent cells. Subsequently, 50 ml SLM17 or SGM17 broth supplemented with 1% glycine (NZ9000) 2% (100-E) or 0.8% (100-F) threonine were inoculated (2%) with the appropriate strain and incubated until an $OD_{600\ nm}$ of approximately 0.5 was reached. In the case of 100-E, ampicillin (Sigma-Aldrich, Germany) was added to a final concentration of 20 µg/ml, and incubation continued for a further 1 hour. All steps from this point onward were performed at either 4° C. or on ice. The cells were centrifuged at 4500 rpm for 15 minutes to pellet and the supernatant discarded. The cells were then washed twice in 15 ml ice cold 0.5 M sucrose/10% glycerol (Sigma-Aldrich, Germany; SG) solution. Finally, the cells were resuspended in 1 ml SG and 100 µl aliquots were immediately stored at −80° C. until electrotransformation as described below.

7. Construction of Antisense Plasmid Vectors

The PCR primers used to amplify cas7, csn2 or cas9 from either *S. thermophilus* 100-E or 100-F are listed in Table 2, and were designed to incorporate the entire relevant gene including the Shine-Dalgarno (SD) sequence. To ensure that an antisense product was produced, all cas genes were cloned into the pNZ44 plasmid (containing a chloramphenicol resistance gene marker) in the reverse orientation relative to the p44 promoter, as described by McGrath, et al. (2001). In the case of pNZ44+100-F2Casi, the csn2 gene was cloned directly behind the p44 promoter, followed by cas7, whereas in the pNZ44+100-F2CasSWi construct, cas7 was cloned directly behind the p44 promoter followed by csn2. Firstly, the appropriate cas gene product was PCR amplified from *S. thermophilus* 100-E or 100-F. The PCR conditions were as follows: 95° C.×10 min, followed by 30 cycles of 95° C.×15 s, 55° C.×15 s and 72° C. for either 3 min 15 s (cas9) or 1 min 10 s (cas7, csn2) with a final extension step of 72 ° C. for 10 min. The products were then purified using the JetQuick PCR product purification kit (Genomed, Germany). pNZ44 plasmid DNA was isolated from *Lactococcus lactis* NZ9000::pNZ44 using the GeneJet plasmid Miniprep kit (Thermo Scientific, U.S.A.). PCR products and plasmid were restricted separately ON at room temperature (RT) using the restriction enzymes (Roche, Germany) PstI and either NcoI (100-E-derived cas7) or XbaI (100-E-derived cas9). The reaction mixture was as follows: 50 µl plasmid/product, 2 µl each restriction enzyme, 20 µl buffer H (Roche, Germany), 126 µl $H_2O$). Restricted products were subjected to electrophoretic examination to check their integrity and to estimate relative amounts (for ligation, an approximate insert to vector ratio of 4:1 was considered ideal). Ligation of insert and vector was performed by incubating 1 µl T4 DNA ligase (Roche, Germany), 1 µl ligase buffer (Roche, Germany), 6 µl insert and 2 µl vector ON at RT. For constructs pNZ44+100-F2Casi and pNZ44+100-F2CasSWi, 3 µl of each appropriate insert was used in the ligation reaction. Antisense constructs used in this study are listed in Table 3.

TABLE 3

Antisense constructs used in this study

| Antisense construct | Target | Source |
|---|---|---|
| pNZ44 + 100-ECas7i | 100-E CRISPR1-cas7 | This study |
| pNZ44 + 100-ECas9i | 100-E CRISPR1-cas9 | " |
| pNZ44 + 100-FCas7i | 100-F CRISPR1-Cas7 | " |
| pNZ44 + 100-FCas9i | 100-F CRISPR1-Cas9 | " |
| pNZ44 + 100-F2Casi | 100-F CRISPR3-Csn2 and CRISPR1-Cas7 | " |

TABLE 3-continued

Antisense constructs used in this study

| Antisense construct | Target | Source |
|---|---|---|
| pNZ44 + 100-F2CasSWi | 100-F CRISPR1-Cas7 and CRISPR3-Csn2 | " |

8. Electrotransformation & Transformant Selection

Prior to transformation, constructs were dialysed using 0.025 µm MF membrane filters (Merck Millipore, Germany) for 10 mins against sdH$_2$O. All constructs were generated in *L. lactis* NZ9000 prior to their subsequent transfer to *S. thermophilus* 100-E or 100-F. Electrotransformation was performed using freshly prepared competent cells as described above, with the following modifications: competent cells were defrosted on ice for 5 mins, 10 µl construct was added and the solution was gently mixed. The mixture was transferred to a pre-chilled 2 mm electroporation cuvette (Cell Projects, U.K.) and electroporated under the following conditions: 1.75 kV (*S. thermophilus*) or 2.0 kV (*L. lactis*)/200 ohm/25 µF. 950 µl recovery broth (LM17 or GM17 with the addition of 20 mM MgCl$_2$ and 2 mM CaCl$_2$ (Sigma-Aldrich, Germany)) was immediately added and the transformed cells were recovered at 30° C. (*L. lactis*) or 42° C. (*S. thermophilus*) for 2.5 hrs. 100 µl of undiluted and, where appropriate, diluted transformed cells were plated on antibiotic selection plates (LM17 or GM17 containing 5 µg/ml chloramphenicol (Sigma-Aldrich, Germany); L/GM17+Cm5) and incubated ON at the appropriate temperature. Colonies representing potential transformants were screened by PCR using a forward primer designed upstream of the multiple cloning site (MCS) of plasmid pNZ44 and the appropriate 'forward' insert primer (Table 2), to reduce the incidence of false positive detection. Presumed transformants were purified on LM17+Cm5 agar plates and subjected to CRISPR sequencing, phage sensitivity assays (as described above) and plasmid sequencing, which was performed using primers designed outside the MCS of pNZ44 (pNZ44fwd and rev; Table 2).

9. Plasmid Curing

In order to cure introduced pNZ44 and pNZ44-derivative vectors, selected transformants were subjected to four ON passages at 42° C. in LM17 without the addition of chloramphenicol. Overnight cultures were then ten-fold serially diluted in ¼ strength Ringers solution (Merck, Germany), or a plate streak performed, and individual colonies were assessed for sensitivity to chloramphenicol by streaking on LM17+Cm5 agar plates. Streaked colonies which showed no growth on LM17+Cm5 but growth on LM17 were defined as presumptive cured transformants and subjected to validation by CRISPR PCR and plasmid preparation as described above.

10. Sedimentation Assays

*S. thermophilus* strains were routinely grown from 10% glycerol stocks, 20% Reconstituted Skimmed Milk (RSM) stocks or from single colonies overnight at 42° C. in LM17 broth (as described in section 1 of the MATERIALS AND METHODS). The parent strains and BIMs were treated identically and after overnight incubation at 42° C., visual assessment of the cultures was performed to observe the growth characteristic of the cultures in broth. Only if the cultures were consistently observed to sediment to the base of the tube or along the wall of the tube was the phenotype considered relevant. In all cases, the parent strain was observed to sediment to a markedly reduced degree after overnight growth. For the optical density assay, the OD600$_{nm}$ of 1 ml of each culture (taken from the top of the test tube) after ON incubation was measured using a DU 730 spectrophotometer (Beckman Coulter, U.S.A.).

11. Microscopic Assays

Morphological assessment and comparison of the parent strains and derived BIMs was performed via wet mount. 5 µl of fresh overnight culture was placed on a glass slide (in duplicate) and a cover slip immediately placed on top of the sample. Each sample was then visualised under 63× magnification using a confocal laser scanning microscope and a Zeiss LSM 5 Exciter (Carl Zeiss, Jena, Germany; excitation 488 nm). The percentage increase in chain length or cells per chain (CPC) of derived BIMs relative to the parent strains was calculated firstly by determining the average number of individual cells per chain in all samples by counting at least 20 chains per strain. The average increase in length was then expressed as a percentage using the following formula: $(CPC_{mutant}-CPC_{parent})/CPC_{parent}\times 100\%$). In this and all cases, the unpaired student t-test was used to determine significant differences between the parent and derived BIMs datasets.

12. Heap Lawrence Assay

The phage resistance robustness was assessed using a so called "Heap-Lawrence" assay as follows. An overnight (ON) culture of the strains to be assessed (wild type plus BIMs) was made by inoculating 250 µL of 10% RSM with 50 uL stock culture and incubated O/N at 42° C. The next day, the ON culture was diluted 5 times with fresh 10% RSM, 50 µl diluted culture was added to an MTP containing 650 µl 10% RSM. Cells were allowed to grow for 1 hour and then a high titer phage lysate was added. Strain and phage were incubated at 42° C. Acidification was monitored after 6-8 hrs after which strains and phage were left ON. The next day MTPs were centrifuged at 4000 rpm for 10 minutes and supernatant, containing the phages, was transferred to a greiner tube. Part of the supernatant was mixed 1:1 with phage lysate in a new tube. This phage-mix was then used as a source of phage in another round of Heap-Lawrence as described for day 2. The procedure was repeated for many cycles, thereby allowing the phages to adept to overcome the strain's phage resistance. By monitoring the number of cycles it takes for a phage to become virulent (indicated by the inability of the strains to acidify the milk) an indication of the phage robustness is obtained.

EXAMPLES

Example 1

CRISPR silencing of Parent and Bacteriophage Insensitive Mutants (BIMs) of *S. thermophilus* 100-E 1. Cas9 Silencing in *S. thermophilus* 100-E BIMs 1.1. Generation and Analysis of 100-E CRISPR and non-CRISPR BIMs Bacteriophages against *S. thermophilus* 100-E (4 in total) and BIMs against these phages were isolated as described in the MATERIALS AND METHODS. Two BIMs, *S. thermophilus* BIM100-E-D1A-L5 and BIM100-E-D1A-L7, were selected for further analysis by plaque assay and CRISPR sequencing, the results of which are shown in Tables 4 and 5, respectively.

TABLE 4

Relative efficiencies of plaquing (EOP) of phages of
Streptococcus thermophilus strain 100-E and derived BIMs.

| Parent/BIM | Phage | | | |
|---|---|---|---|---|
| | φ100-E-D1A-L | φ100-E-D2A-L | φ100-E-D3A-L | φ100-E-D4A-L |
| 100-E (parent) | 1 | 1 | 1 | 1 |
| BIM100-E-D1A-L5 | $1.1 \pm 1.9 \times 10^{-6}$ | $\leq 1 \times 10^{-7}$ | $\leq 1 \times 10^{-7}$ | $\leq 1 \times 10^{-7}$ |
| BIM100-E-D1A-L7 | $8.67 \pm 0.15 \times 10^{-8}$ | $0.64 \pm 0.13$ | $0.85 \pm 0.17$ | $0.51 \pm 0.04$ |

Note 1:
$\leq$ denotes the limit of detection i.e. no plaques were detected when the derived BIM was challenged with a phage lysate containing $1 \times 10^7$ pfu/ml phages.

Note 2:
In derived BIM nomenclature, D1A-L denotes the phage against which the BIM was generated.

TABLE 5

Summary of CRISPR repeat/spacer loci content in *S. thermophilus* strain 100-E and derived BIMs.

| Parent/BIM | CRISPR | Size (bp) | Direct repeat | # spacers | Terminal repeat |
|---|---|---|---|---|---|
| 100-E (parent) BIM100-E-D1A-L5 BIM100-E-D1A-L7 | 1 | 2409 2409 2476 | 5'-GTTTTTGTACTCT CAAGATTTAAGT AACTGTACAAC-3' SEQ ID. No 30 | 36 36 37 | 5'-GTTTTTGTACTCT CAAGATTTAAGTA ACTGTACAGT-3' SEQ ID. No 31 |
| 100-E (parent) BIM100-E-D1A-L5 BIM100-E-D1A-L7 | 2 | 115 | 5'-GATATAAACCTA ATTACCTCGAGA GGGGACGGAAA C -3' SEQ ID. No 32 | 1 | 5'-GATATAAACCTAA TTACCTCGAGAG GGGACTTTTT-3 SEQ ID. No 33 |
| 100-E (parent) BIM100-E-D1A-L5 BIM100-E-D1A-L7 | 3 | 1358 | 5'-GTTTTAGAGCTG TGTTGTTTCGAAT GGTTCCAAAAC -3' SEQ ID. No 34 | 20 | As direct repeat |

The above results show that the mechanisms responsible for φ100-E-D1A-L resistance in BIM100-E-D1A-L5 and BIM100-E-D1A-L7 are different.

BIM100-E-D1A-L5 can be defined as a 'non-CRISPR BIM' due to the fact that CRISPR repeat/spacer locus is 100% identical to the parent strain in the three loci sequenced (table 5), combined with the apparent absence of any additional CRISPR-Cas loci on the whole sequenced genome. In addition, the sedimentation profile (FIG. 5; Table 11), typified here (and in all cases) by cell aggregation at the bottom of the ON culture tube, and relative increase of cell chain length (FIG. 6; Table 10) indicate that this BIM has undergone a mutation in a phage receptor that is a component of the cell envelope.

In the case of BIM100-E-D1A-L7, it was concluded that insensitivity to φ100-E-D1A-L was conferred by the CRISPR mechanism, due to the addition of one spacer at the leader end of the CRISPR1 repeat/spacer locus (Table 5). This 30 bp spacer showed 100% homology to a region spanning the start codon of a gene coding for a RecT recombinase protein on the genome of phage φ100-E-D1A-L, which was used in the challenge. This exact 30 bp segment was not found in the genomes of any of the other three phages infecting *S. thermophilus* 100-E (data not shown). This conclusion is supported by the complete absence in BIM100-E-D1A-L7 of the distinctive sedimentation profile (FIG. 5; Table 11), and cell chain length increase (FIG. 6, Table 10), indicative of a mutation in a component of the cell envelope (as seen in BIM100-E-D1A-L5 and double hurdle BIMs below).

1.2. Transformation, Curing & Phage Sensitivities of BIM100-E-DIA-L5 and BIM100-E-D1A-L7

*S. thermophilus* BIM100-E-D1A-L5 and BIM100-E-D1A-L7 were transformed using freshly isolated pNZ44+ 100-ECas9i and pNZ44, pNZ44+100-ECas7i and pNZ44+ 100-ECas9i, respectively, and potential transformants were screened using the confirmatory PCR as described in the MATERIALS AND METHODS. Four presumptive transformants, BIM100-E-D1A-L5::pNZ44+100-ECas9i (non-CRISPR control), BIM100-E-D1A-L7::pNZ44 (plasmid control), BIM100-E-D1A-L7::pNZ44+100-ECas7i (for use in 'double hurdle' BIM generation, see section 1.3) and BIM100-E-D1A-L7::pNZ44+100-ECas9i (proof of principle) were selected for validation and further analysis.

BIM100-E-D1A-L5::pNZ44+100-ECas9i and BIM100-E-D1A-L7::pNZ44+100-ECas9i were subjected to plasmid preparation (FIG. 1), pNZ44 MCS PCR (FIG. 2), GTG RAPD typing PCR (FIG. 3) and CRISPR PCR (FIG. 4) followed by sequencing, as well as plasmid sequencing for validation purposes and as described in the MATERIALS AND METHODS. Electrophoretic examination of the plasmid preparation (FIG. 1) clearly showed that plasmid DNA, presumed to be pNZ44+100-ECas9i, had been introduced to BIM100-E-D1A-L5 and BIM100-E-D1A-L7 compared to the parent and original BIMs which showed no native or introduced plasmids. The MCS of pNZ44 in both the original plasmid and antisense constructs were also amplified (FIG. 2) and showed a clear difference in size, the difference corresponding to the size of the *S. thermophilus* 100-E cas9 gene. The purified plasmid DNA was subsequently subjected to sequencing as described in the MATERIALS AND METHODS, and showed the addition of the *S. thermophilus* 100-E cas9 gene in the reverse orientation between the PstI and XbaI restriction sites on the pNZ44 plasmid vector in both transformants. Finally, the CRISPR loci of BIM100-

E-D1A-L5::pNZ44+100-ECas9i and BIM100-E-D1A-L7::pNZ44+100-ECas9i were amplified (FIG. 4) and subjected to sequencing. The CRISPR spacer content of each transformant was 100% identical to each respective original BIM, confirming direct derivation.

The BIM100-E-D1A-L5::pNZ44+100-ECas9i and BIM100-E-D1A-L7::pNZ44+100-ECas9i transformants were subjected to phage sensitivity assays as described in the MATERIALS AND METHODS, the results of which are shown in Table 6. The results clearly show the suppression of acquired phage-resistance from BIM100-E-D1A-L7::pNZ44+100-ECas9i, despite the retention of the effective extra CRISPR spacer mentioned above. This suppression of resistance was not observed for BIM100-E-D1A-L5::pNZ44+100-ECas9i, highlighting the CRISPR1 independence of the BIM100-E-D1A-L5 mechanism of phage-resistance.

TABLE 6

Relative efficiencies of plaquing (EOP) of phages of *Streptococcus thermophilus* strain 100-E, derived BIM and transformant.

| Parent/BIM/Transformant | Phage | | | |
|---|---|---|---|---|
| | φ100-E-D1A-L | φ100-E-D2A-L | φ100-E-D3A-L | φ100-E-D4A-L |
| 100-E (parent) | 1 | 1 | 1 | 1 |
| BIM100-E-D1A-L7 | $8.67 \times 10^{-8} \pm 1.5 \times 10^{-7}$ | $0.64 \pm 0.13$ | $0.85 \pm 0.17$ | $0.51 \pm 0.04$ |
| BIM100-E-D1A-L7::pNZ44 | $4.87 \times 10^{-6} \pm 7.37 \times 10^{-7}$ | $3.82 \pm 0.87$ | $6.02 \pm 0.83$ | $5.18 \pm 1.23$ |
| BIM100-E-D1A-L7::pNZ44 + 100-ECas9i | $1.02 \pm 0.04$ | $1.09 \pm 0.32$ | $0.93 \pm 0.09$ | $1.43 \pm 0.36$ |
| BIM100-E-D1A-L7::pNZ44 + 100-ECas9i (Cured) | $2.22 \times 10^{-6} \pm 3.71 \times 10^{-6}$ | $2.69 \pm 1.14$ | $2.83 \pm 1.37$ | $0.28 \pm 0.27$ |
| BIM100-E-D1A-L5 | $1.1 \times 10^{-6} \pm 1.9 \times 10^{-6}$ | $\leq 1 \times 10^{-7}$ | $\leq 1 \times 10^{-7}$ | $\leq 1 \times 10^{-7}$ |
| BIM100-E-D1A-L5::pNZ44 + 100-ECas9i | $1.22 \times 10^{-6} \pm 1.5 \times 10^{-6}$ | $\leq 1 \times 10^{-7}$ | $1.85 \times 10^{-7} \pm 3.21 \times 10^{-7}$ | $\leq 1 \times 10^{-7}$ |

The BIM100-E-D1A-L7::pNZ44+100-ECas9i transformant was then subjected to plasmid curing as described in the MATERIALS AND METHODS. Upon electrophoretic examination, the cured derivative showed an identical plasmid content of the parent S.thermophilus 100-E and original BIMs (i.e. no native or introduced plasmids; FIG. 1).

The cured derivative was then subjected to phage sensitivity assays as described (Table 6), the results of which show the restoration of acquired resistance to φ100-E-D1A-L of the original BIM100-E-D1A-L7.

1.3—Reduction in CRISPR-Mediated BIM Incidence in 100-E BIM Generation

In order to reduce the incidence of CRISPR spacer alterations during BIM generation, *S. thermophilus* 100-E (parent) was transformed with freshly isolated pNZ44+100-ECas7i or pNZ44+100-ECas9i DNA, and Cm-resistant transformants were screened as described in the MATERIALS AND METHODS. BIM generation was performed, presumed BIMs purified and CRISPRs 1 and 3 amplified as described in the MATERIALS AND METHODS. CRISPR2 was omitted from this experiment due to its apparent redundancy in *S. thermophilus*, and only the leader end of each locus was sequenced due to the significant bias in iterative spacer incorporation in the remaining two CRISPR systems (Horvath et al., 2008). Sequencing was performed from the leader end of the CRISPR 1 and 3 loci of a total of 90 presumed BIMs (30 derived using 100-E parent, 30 using 100-E::pNZ44+100-ECas7i and 30 using 100-E:: pNZ44+100-ECas9i—10 BIMs each being derived from three separate experiments), using the forward primers shown in Table 2 (Seq IDs 1, 7, and 9). At least 800 bp (CRISPR1) or 500 bp (CRISPR3) was sequenced for each potential BIM. Two CRISPR3 sequences were omitted due to poor data. The results of the cas-silenced BIM generation experiment are summarised in Table 7.

TABLE 7

Summary of CRISPR alterations in in presumed BIMs generated using *S. thermophilus* 100-E parent and cas7 and cas9 silenced strains.

| Potential BIMs origin | CRISPR alterations | | |
|---|---|---|---|
| | # CRISPR1 | # CRISPR3 | # None |
| 100-E Parent | 6 (20%) | 0 (0%) | 24 (80%) |
| 100-E::pNZ44 + 100-ECas7i | 0 (0%) | 2 (6.7%) | 28 (93.3%) |

TABLE 7-continued

Summary of CRISPR alterations in in presumed BIMs generated using *S. thermophilus* 100-E parent and cas7 and cas9 silenced strains.

| Potential BIMs origin | CRISPR alterations | | |
|---|---|---|---|
| | # CRISPR1 | # CRISPR3 | # None |
| 100-E::pNZ44 + 100-ECas9i | 0 (0%) | 0 (0%) | 28 (100%) |

It is clear from the above results that there is a significant reduction in the incidence of CRISPR alterations in derived BIMs of 100-E using both the cas7 and cas9 silenced transformants. It should be noted that both silencing constructs are designed to act on cas genes associated with CRISPR1—for this reason some transference of activity to CRISPR3 (as shown by the slight increase in CRISPR3 alterations) can be explained.

1.4—Generation of a 'Double Hurdle' BIM of *S. thermophilus* 100-E

In order to obtain BIMs of 100-E that are phage resistant due to both the mechanism of action of the CRISPR system and by a presumed mutation in a component of the cell envelop that acts as a phage receptor, so called 'double hurdle' (DH) BIMs of 100-E were generated (BIM100-E-DH51 and BIM100-E-DH61; Table 1). BIM100-E-D1A-L7 was considered to be a 'pure' CRISPR-mediated BIM, owing to the effectiveness of the CRISPR silencing method in restoring sensitivity to φ100-E-D1A-L (Table 6). For this reason, BIM100-E-D1A-L7 was applied in the generation of the DH BIMs.

It is clear from Table 6 that the CRISPR mechanism provides BIM100-E-D1A-L7 with resistance against φ100-E-D1A-L only, while φ100-E-D2A-L, φ100-E-D3A-L and φ100-E-D4A-L retain the ability to infect the BIM. This sensitivity was exploited during DH BIM generation. BIM100-E-D1A-L7 was firstly transformed with the Cas7 silencing plasmid, pNZ44+100-ECas7i (Table 3; FIG. 7), to increase the frequency of secondary non-CRISPR BIM selection. The BIM was then subjected to a phage challenge using φ100-E-D2A-L and a number of potential BIMs were purified as described in the MATERIALS AND METHODS. Selected potential BIMs were screened on the basis of phage sensitivity and CRISPR sequences as well as sedimentation profile and chain length which are indicators of potential cell wall mutation-harbouring BIMs. Double Hurdle BIMs were subjected to plasmid curing (FIG. 7) as described above prior to phage sensitivity assays.

TABLE 10

Relative cells per chain (CPC) of parent and BIMs of *S. thermophilus* strain 100-E.

| Strain | CPC (cells) | % CPC average versus parent | p-value |
| --- | --- | --- | --- |
| 100-E (parent) | 10.84 ± 8.64 | N/A | N/A |
| BIM100-E-D1A-L7 | 7.4 ± 8.30 | 68.3 | 0.12 |
| BIM100-E-D1A-L5 | 25.9 ± 13.0 | 238.9 | $3.9 \times 10^{-5}$ |
| BIM100-E-DH51 | 19.44 ± 13.9 | 179.4 | 0.012 |
| BIM100-E-DH61 | 35.88 ± 25.5 | 330.9 | $3.9 \times 10^{-5}$ |

BIM100-E-DH51 and BIM100-E-DH61 can be defined 'double hurdle' BIMs for two reasons. Firstly, all three CRISPR repeat/spacer loci sequenced were found to be 100% identical to BIM100-E-D1A-L7 (Table 8), combined with the apparent absence of any additional CRISPR-Cas loci on the genome. This indicates that a mechanism other than the CRISPR system provided the additional resistance to phages φ100-E-D2A-L, φ100-E-D3A-L and φ100-E-D4A-L which was not observed in BIM100-E-D1A-L7. In addition, the sedimentation profile (FIG. 8; Table 11) and relative increase of cell chain length (FIG. 6; Table 10) indicate that these BIMs have undergone a mutation in cell envelope component that acts as a phage receptor. The combination of the CRISPR and non-CRISPR 'hurdles' to phage infection in one strain in this case leads to the definition of double hurdle BIMs.

TABLE 8

Summary of CRISPR repeat/spacer loci content in *S. thermophilus* strain 100-E and derived BIMs.

| Parent/BIM | CRISPR | Size (bp) | Direct repeat | # spacers | Terminal repeat |
| --- | --- | --- | --- | --- | --- |
| 100-E (parent)<br>BIM100-E-D1A-L7<br>BIM100-E-DH51<br>BIM100-E-DH61 | 1 | 2409<br>2476 | 5'-GTTTTTGTACTCTCCAAGATTTAAGTAACTGTACAAC-3'<br>SEQ ID. No 30 | 36<br>37 | 5'-GTTTTTGTACTCTAAGATTTAAGTAACTGTACAGT-3'<br>SEQ ID. No 31 |
| 100-E (parent)<br>BIM100-E-D1A-L7<br>BIM100-E-DH51<br>BIM100-E-DH61 | 2 | 115 | 5'-GATATAAACCTAATTACCTCGAGAGGGGACGGAAAC -3'<br>SEQ ID. No 32 | 1 | 5'-GATATAAACCTAATTACCTCGAGAGGGGACTTTTT-3<br>SEQ ID. No 33 |
| 100-E (parent)<br>BIM100-E-D1A-L7<br>BIM100-E-DH51<br>BIM100-E-DH61 | 3 | 1358 | 5'-GTTTTAGAGCTGTGTTGTTTCGAATGGTTCCAAAAC -3'<br>SEQ ID. No 34 | 20 | As direct repeat |

TABLE 9

Relative efficiencies of plaquing (EOP) of phages of *Streptococcus thermophilus* strain 100-E and derived BIMs.

| Parent/BIM | Phage | | | |
| --- | --- | --- | --- | --- |
| | φ100-E-D1A-L | φ100-E-D2A-L | φ100-E-D3A-L | φ100-E-D4A-L |
| 100-E (parent) | 1 | 1 | 1 | 1 |
| BIM100-E-D1A-L7 | $8.67 \pm 0.15 \times 10^{-8}$ | 0.64 ± 0.13 | 0.85 ± 0.17 | 0.51 ± 0.04 |
| BIM100-E-DH51 | $\leq 10^{-9}$ | $1.93 \pm 1.32 \times 10^{-4}$ | $2.19 \pm 1.08 \times 10^{-5}$ | $\leq 10^{-6}$ |
| BIM100-E-DH61 | $\leq 10^{-9}$ | $3.21 \pm 1.02 \times 10^{-4}$ | $2.71 \pm 1.73 \times 10^{-5}$ | $\leq 10^{-6}$ |

Note 1:
≤ denotes the limit of detection i.e. no plaques were detected when the derived BIM was challenged with a phage lysate containing $1 \times 10^9$ pfu/ml phages.

Note 2:
In derived BIM nomenclature, D1A-L denotes the phage against which the BIM was generated.

TABLE 11

Optical densities of *S. thermophilus* 100-E and derived BIMs overnight broth cultures.

| Strain | $OD600_{nm}$ of broth after ON incubation | $OD600_{nm}$ as % of WT |
| --- | --- | --- |
| 100-E WT | .667 ± .010 | N/A |
| BIM100-E-D1A-L7 | .886 ± .068 | 132.8 |
| BIM100-E-D1A-L5 | .065 ± .061 | 9.7 |
| BIM100-E-DH51 | .087 ± .023 | 12.9 |
| BIM100-E-DH61 | .034 ± .008 | 5.0 |

1.5—Heap Lawrence Assy of a 'Double Hurdle' BIM of *S. thermophilus* 100-E

To test the phage robustness of a provided CRISPR BIM, a non CRISPR BIM and a double hurdle (DH) BIM's, the BIM's were subjected to a Heap Lawrence assay against phage φ100-E-D1A-L as described in the MATERIALS AND METHODS, the results of which are shown in table 12 below.

TABLE 12 summary Heap Lawrence data against phage φ100-E-D1A-L

| NAME | TYPE | 1 | 2 | 3 | 4 |
|---|---|---|---|---|---|
| BIM100-E-D1A-L7 | CRISPR | + | + | − | − |
| BIM100-E-D1A-L5 | NON-CRISPR | + | + | + | − |
| BIM100-E-DH51 | DH | + | + | + | + |
| BIM100-E-DH61 | DH | + | + | + | + |

It is clear from the above results that an increased phage robustness is obtained for a non CRISPR BIM BIM100-E-D1A-L5 in view of CRISPR BIM BIM100-E-D1A-L7. Further, the above results show that a double hurdle BIM BIM100-E-DH51 and BIM100-E-DH61 provide a further increased phage robustness. In other words, the combination of different phage resistant mechanisms works synergistically by increasing the phage robustness to phage φ100-E-D1A-L.

Example 2

CRISPR silencing of Parent and Bacteriophage Insensitive Mutants (BIMs) of *S. thermophilus* 100-F 2. Silencing of cas9 in *S. thermophilus* 100-F BIMs 2.1. Generation and Analysis of 100-F CRISPR BIMs Bacteriophages against *S. thermophilus* 100-F (3 in total; Table 1) and BIMs against these phages were isolated as described in the MATERIALS AND METHODS. One BIM, *S. thermophilus* BIM100-F-NGBD1A-L2 was selected for further analysis by plaque assay and CRISPR sequencing, the results of which are shown in Tables 13 and 14, respectively.

TABLE 13

Relative efficiencies of plaquing (EOP) of phages of *Streptococcus thermophilus* strain 100-F and derived BIMs.

| Parent/BIM/Transformant | Phage | | |
|---|---|---|---|
| | φSTV84-D1A-L | φSTV88-D1A-L | φNGB-D1A-L |
| 100-F (parent) | 1 | 1 | 1 |
| BIM100-F-NGBD1A-L2 | $4.04 \times 10^{-6} \pm 6.41 \times 10^{-7}$ | $\leq 10^{-7}$ | $3.97 \times 10^{-6} \pm 2.13 \times 10^{-6}$ |

TABLE 14

Summary of CRISPR repeat/spacer loci content in *S. thermophilus* strain 100-F and derived BIMs.

| Parent/BIM | CRISPR | Size (bp) | Direct repeat | # spacers | Terminal repeat |
|---|---|---|---|---|---|
| 100-F (parent) BIM100-F-NGBD1A-L2 BIM100-F-NGBD1A-L2::pNZ44 BIM100-F-NGBD1A-L2::pNZ44 + 100-FCas9i BIM100-F-NGBD1A-L2 (cured) | 1 | 2147 2212 | 5'-GTTTTTGTACTCT CAAGATTTAAGT AACTGTACAAC-3' SEQ ID. No 30 | 32 33 | 5'-GTTTTTGTACTC TCAAGATTTAAG TAACTGTACAGT-3' SEQ ID. No 31 |
| 100-F (parent) BIM100-F-NGBD1A-L2 BIM100-F-NGBD1A-L2::pNZ44 BIM100-F-NGBD1A-L2::pNZ44 + 100-FCas9i BIM100-F-NGBD1A-L2 (cured) | 2 | 258 | 5'-GATATAAACCTA ATTACCTCGAGA GGGGACGGAAA C -3' SEQ ID. No 32 | 3 | 5'-GATATAAACCTA ATTACCTCGAG AGGGGACTTTT TT-3' SEQ ID. No 33 |
| 100-F (parent) BIM100-F-NGBD1A-L2 BIM100-F-NGBD1A-L2::pNZ44 BIM100-F-NGBD1A-L2::pNZ44 + 100-FCas9i BIM100-F- | 3 | 827 | 5'-GTTTTAGAGCTG TGTTGTTTCGAAT GGTTCCAAAAC -3' SEQ ID. No 34 | 12 | As direct repeat |

TABLE 14-continued

Summary of CRISPR repeat/spacer loci content in S. thermophilus strain 100-F and derived BIMs.

| Parent/BIM | Size CRISPR (bp) | Direct repeat | # spacers | Terminal repeat |
|---|---|---|---|---|
| NGBD1A-L2 (cured) | | | | |
| 100-F (parent) BIM100-F-NGBD1A-L2 BIM100-F-NGBD1A-L2::pNZ44 BIM100-F-NGBD1A-L2::pNZ44 + 100-FCas9i BIM100-F-NGBD1A-L2 (cured) | 4 | 762 | 5'-GTTTTTCCCGCACACGCGGGGTGATCC - '3 SEQ ID. No 35 | 12 | 5'-GTTTTTCCCGCACACGCGGGGTGATTC - 3' SEQ ID. No 36 |

The above results indicate that the observed insensitivity of BIM100-F-NGBD1A-L2 to at least two of the three 100-F phages was conferred by the CRISPR mechanism, due to the addition of one spacer at the leader end of the CRISPR1 repeat/spacer locus. This 30 bp spacer showed 100% homology to a region in a hypothetical protein in the replication modules of phages φSTV84-D1A-L and φNGB-D1A-L (which was used in the challenge). The genome of φSTV88-D1A-L was not available for analysis in this manner.

2.2. Transformation, Curing & Phage Sensitivities of BIM100-F-NGBD1A-L2

S. thermophilus BIM100-F-NGBD1A-L2 was transformed using freshly isolated pNZ44 and pNZ44+100-FCas9i, and Cm-resistant transformants were screened and then checked using the confirmatory PCR as described in the MATERIALS AND METHODS. Two presumptive transformants, BIM100-F-NGBD1A-L2::pNZ44 (plasmid control) and BIM100-F-NGBD1A-L2::pNZ44+100-FCas9i (proof of principle) were selected for validation and analysis.

BIM100-F-NGBD1A-L2::pNZ44 and BIM100-F-NGBD1A-L2::pNZ44+100-FCas9i were subjected to plasmid preparation followed by sequencing, pNZ44 MCS PCR (FIG. 11), CRISPR PCR followed by sequencing (Table 14) and plasmid sequencing for validation purposes and as described in the MATERIALS AND METHODS. PCR amplification of the pNZ44 MCS regions of all strains (FIG. 12) clearly showed that an approximately 500 bp product, presumed to be the MCS region of pNZ44 had been introduced to BIM100-F-NGBD1A-L2 compared to the parent original BIM which showed no native or other introduced plasmid products. The MCS of pNZ44 in both the original plasmid and antisense constructs were also amplified (FIG. 11) and showed a clear difference in size, the difference corresponding to the size of the S. thermophilus 100-F cas9 gene. The purified plasmid DNA was subsequently subjected to sequencing as described in the MATERIALS AND METHODS, and showed the addition of the S. thermophilus 100-F cas9 gene in the reverse orientation between the PstI and XbaI restriction sites on the pNZ44 plasmid vector in both transformants. Finally, the CRISPR loci of BIM100-F-NGBD1A-L2::pNZ44 and BIM100-F-NGBD1A-L2::pNZ44+100-FCas9i were amplified and subjected to sequencing. The CRISPR spacer content of each transformant was 100% identical to BIM100-F-NGBD1A-L2, confirming direct derivation. This was also confirmed by GTG RAPD PCR profiling (FIG. 10).

The BIM100-F-NGBD1A-L2::pNZ44 and BIM100-F-NGBD1A-L2::pNZ44+100-FCas9i transformants were subjected to phage sensitivity assays as described in the MATERIALS AND METHODS, the results of which are shown in Table 15. The results clearly show the suppression of acquired phage-resistance of BIM100-F-NGBD1A-L2::pNZ44+100-FCas9i, despite the retention of the CRISPR spacer mentioned above. This suppression of resistance was not observed for phage φSTV88-D1A-L. Due to the the unavailability of the complete genome sequence of this phage, it was not possible to confirm the presence of identical protospacer sequence on the genome. Considering the absence of any additional spacers in the CRISPR2, CRISPR3 or CRISPR4 loci, it is probable that the resistance of BIM100-F-NGBD1A-L2 to φSTV88-D1A-L is conferred by a mechanism other than CRISPR.

TABLE 15

Transformation, curing & phage sensitivities of CRISPR and silenced CRISPR BIMs of 100-F

| Parent/BIM/Transformant | Phage | | |
|---|---|---|---|
| | φSTV84-D1A-L | φSTV88-D1A-L | φNGB-D1A-L |
| 100-F (parent) | 1 | 1 | 1 |
| BIM100-F-NGBD1A-L2 | $4.04 \times 10^{-6} \pm 6.41 \times 10^{-7}$ | $\leq 10^{-7}$ | $3.97 \times 10^{-6} \pm 2.13 \times 10^{-6}$ |
| BIM100-F-NGBD1A-L2::pNZ44 | $6.04 \times 10^{-6} \pm 5.49 \times 10^{-7}$ | $\leq 10^{-7}$ | $5.95 \times 10^{-6} \pm 1.42 \times 10^{-6}$ |

TABLE 15-continued

Transformation, curing & phage sensitivities
of CRISPR and silenced CRISPR BIMs of 100-F

| Parent/BIM/Transformant | Phage | | |
|---|---|---|---|
| | φSTV84-D1A-L | φSTV88-D1A-L | φNGB-D1A-L |
| BIM100-F-NGBD1A-L2::pNZ44 + 100-FCas9i | 0.08 ± 0.07 | $1.02 \times 10^{-5}$ ± $9.34 \times 10^{-7}$ | 0.03 ± 0.007 |
| BIM100-F-NGBD1A-L2::pNZ44 + 100-FCas9i (Cured) | $1.65 \times 10^{-5}$ ± $5.5 \times 10^{-6}$ | $9.52 \times 10^{-7}$ ± $1.35 \times 10^{-6}$ | $4.07 \times 10^{-6}$ ± $2.92 \times 10^{-6}$ |

The BIM100-F-NGBD1A-L2::pNZ44+100-FCas9i transformant was then subjected to plasmid curing as described in the MATERIALS AND METHODS. Upon electrophoretic examination of pNZ44 plasmid MCS PCR products, the cured derivative showed an identical profile of the parent S. thermophilus 100-F and original BIM100-F-NGBD1A-L2 (i.e., no product; FIG. 11). The cured derivative also showed an identical RAPD PCR pattern to its parent BIM (FIG. 10). The cured derivative was then subjected to phage sensitivity assays as described (Table 15), the results of which show the restoration of acquired resistance to φSTV84-D1A-L and φNGB-D1A-L of the original BIM100-F-NGBD1A-L2.

2.3—Simultaneous Silencing of Multiple cas Genes to Achieve Reduced CRISPR-Mediated BIM Incidence During 100-F BIM Generation S. thermophilus 100-F was previously observed to produce a high frequency of CRISPR-mediated BIMs during BIM generation. In order to obtain non-CRISPR-mediated BIMs, the incidence of CRISPR-mediated BIMs in this strain had to be reduced. To this end, plasmids pNZ44+100-FCas7i, pNZ44+100-F2Casi and pNZ44+100-F2CasiSW strain were individually introduced into strain 100-F by electrotransformation and transformants were screened in each case for Cm-resistance, and then verified as described in the MATERIALS AND METHODS. All strains showed an identical GTG RAPD PCR profile (FIG. 12), confirming direct derivation. The results of a pNZ44 MCS confirmatory PCR (FIG. 13) clearly show the introduction of plasmids into respective transformants, with PCR product size correlating with insert size in all cases. BIM generation was performed using these transformants, presumed BIMs purified and CRISPRs 1, 3 and 4 amplified as described in the MATERIALS AND METHODS. As was described for strain 100-E, CRISPR 2 was omitted from this analysis due to its apparent redundancy in S. thermophilus, and only the leader end of each CRISPR locus was sequenced due to the significant bias in iterative spacer incorporation in the remaining two (and, it can be assumed, CRISPR 4) systems (Horvath et al., 2008). Sequencing was performed from the leader end of the CRISPR 1, 3 and 4 loci of a total of 46 presumed BIMs (10 derived from the 100-F parent, 10 from the control strain 100-F:: pNZ44, 6 from the 100-F:: pNZ44+100-FCas7i strain, 10 from the 100-F::pNZ44+100-F2Casi strain, and 10 from the 100-F::pNZ44+100-F2CasiSW strain), using the forward primers shown in Table 2 (Seq IDs 1, 9 and 18). At least 400 bp of each locus was sequenced for each potential BIM, which, combined with GTG RAPD profiling (above), served to confirm direct derivation of each transformant (and BIM) from the parent 100-F strain. The results of the cas-silenced BIM generation experiment are summarised in Table 16.

TABLE 16

Summary of CRISPR alterations in presumed BIMs generated using S. thermophilus
100-F parent and cas7, 2Cas and 2CasSW silenced strains.

| Potential BIMs origin | # BIMs analysed | CRISPR alterations | | | | |
|---|---|---|---|---|---|---|
| | | # CRISPR1 only | # CRISPR3 only | # CRISPR4 only | # CRISPR 1 + 3 | # No alterations |
| 100-F Parent | 10 | 7 (70%) | 1 (10%) | 0 (0%) | 2 (20%) | 0 (0%) |
| 100-F::pNZ4 (plasmid control) | 10 | 7 (70%) | 2 (20%) | 0 (0%) | 1 (10%) | 0 (0%) |
| 100-F::pNZ44 + 100-FCas7i | 6 | 0 (0%) | 4 (66%) | 0 (0%) | 0 (0%) | 2 (33%) |
| 100-F::pNZ44 + 100-F2Casi | 10 | 5 (50%) | 4 (40%) | 0 (0%) | 1 (10%) | 0 (0%) |
| 100-F::pNZ44 + 100-F2CasiSW | 10 | 4 (40%) | 1 (10%) | 0 (0%) | 0 (0%) | 5 (50%) |

In general, it is noteworthy that while BIMs could readily be obtained from 100-F, 100-F plus pNZ44 (plasmid control), 100-F containing plasmid pNZ44+100-F2Casi, and 100-F harbouring plasmid pNZ44+100-F2CasiSW (10 BIMs obtained in approximately 2 rounds of BIM generation), 100F harbouring the silencing plasmid pNZ44+100-FCas7i produced BIMs at a lower frequency which necessitated at least 4 rounds of BIM generation, yielding a total of just 6 BIMs. A possible explanation for this may be the dominance of CRISPR1 activity in 100-F. A dedicated (i.e. single target) antisense construct such as pNZ44+100-FCas7i may lead to a substantial reduction in CRISPR1 activity and hence to a markedly reduced frequency of generated BIMs.

Despite this reduced frequency of BIMs, it is clear from the above results that there is a significant reduction in the incidence (if not a total absence) of CRISPR1 alterations in the examined BIMs obtained when challenging 100-F harbouring the cas7 silencing plasmid. Similar to the results seen for 100-E above (Table 7), transference of activity to CRISPR3 was noted when the CRISPR1 system was effectively disabled by silencing Cas7. In addition, two BIMs were obtained which showed no alterations in CRISPR1, 3 or 4 loci.

BIM generation using the 100-F::pNZ44+100-F2Casi did not appear to have a significant effect on the incidence of CRISPR-mediated BIMs. A possible explanation for this is the location of cas7 (antisense) on the silencing vector—having been cloned behind csn2, its level of effective anti-sense transcripts may have been negatively affected due to, for example, mRNA instability. Considering that spacer addition in CRISPR1 is the most likely adaptation in BIMs generated from phage-challenged 100-F (as evidenced by the proportion of CRISPR1-mediated BIMs derived from 100-F), it may be more effective to silence cas7 by locating it its anti-sense orientation next to the p44 promoter on the silencing construct. This was attempted by switching the locations of cas7 and csn2 in the silencing vector pNZ44+100-F2CasiSW. By using this construct, five BIMs which showed no spacer additions in CRISPR1, 3 or 4 were generated (of ten analysed).

The invention claimed is:

1. A method for the isolation of bacteriophage-insensitive mutants from a *Streptococcus thermophilus* parent strain comprising:
 a. inactivating the CRISPR resistance mechanism of the parent strain;
 b. exposing the parent strain obtained in step a. to a bacteriophage to obtain bacteriophage insensitive mutants;
 c. isolating the bacteriophage insensitive mutants;
 d. comparing the CRISPR loci of the parent strain with the CRISPR loci of the bacteriophage insensitive mutants; and
 e. selecting bacteriophage-insensitive mutants of which the CRISPR loci is identical to the CRISPR loci of the parent strain.

2. The method according to claim 1, comprising, exposing the parent strain obtained in step a. to a single type of bacteriophage.

3. The method according to claim 1, wherein the CRISPR resistance mechanism is inactivated by a method selected from the group consisting of:
 a. introducing into the parent strain one or more DNA constructs comprising a promoter followed by one or more cas genes in the reverse orientation such that the cas gene is transcribed into the corresponding antisense RNA which subsequently binds to the target cas mRNA thereby silencing the cas gene; and
 b. introducing into the parent strain one or more DNA constructs comprising a nucleotide sequence encoding a catalytically inactive Cas9 protein and one or more guide RNAs (sgRNAs) for transcriptional repression of the one or more cas gene(s) in the *Streptococcus thermophilus* parent strain.

4. The method according to claim 3, further comprising removing the DNA construct.

5. The method according to claim 1 wherein the *Streptococcus thermophilus* parent strain is sensitive to the bacteriophage.

6. The method according to claim 1 wherein the *Streptococcus thermophilus* parent strain is insensitive to the bacteriophage.

7. A bacteriophage-insensitive mutant of a *Streptococcus thermophilus* parent strain wherein the CRISPR loci of the bacteriophage-insensitive mutant are identical to the CRISPR loci of the parent *Streptococcus thermophilus* strain, wherein said *Streptococcus thermophilus* parent strain is a strain which was deposited as CBS138555or CBS139996, wherein the bacteriophage-insensitive mutant further comprises a non-CRISPR-mediated bacteriophage resistance, and wherein the bacteriophage-insensitive mutant is obtainable by the method of claim 1.

8. A bacteriophage-insensitive mutant of a *Streptococcus thermophilus* parent strain wherein the CRISPR loci of the bacteriophage-insensitive mutant are not identical to the CRISPR loci of the parent *Streptococcus thermophilus* strain, wherein the bacteriophage-insensitive mutant further comprises a non-CRISPR-mediated bacteriophage resistance, and wherein said *Streptococcus thermophilus* parent strain is a strain which was deposited as CBS138555 or CBS139996.

9. The bacteriophage-insensitive mutant of a *Streptococcus thermophilus* parent strain according to claim 7, wherein the bacteriophage insensitive mutant has an increased sedimentation rate and/or an increased chain formation compared to the *Streptococcus thermophilus* parent strain.

10. A process for production of a dairy product, optionally a fermented milk product or cheese, comprising adding the bacteriophage-insensitive mutant of the *Streptococcus thermophilus* parent strain as defined in claim 8 to a milk product.

11. A process for production of a dairy product, optionally a fermented milk product or cheese, comprising adding the bacteriophage-insensitive mutant of the *Streptococcus thermophilus* parent strain as defined in claim 7 to a milk product.

* * * * *

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial Sequence
<220> FEATURE:
<223> OTHER INFORMATION: primer yc70

<400> SEQUENCE: 1
tgctgagaca acctagtctc tc                                                  22

<210> SEQ ID NO 2
<211> LENGTH: 20
<212> TYPE: DNA
<213> ORGANISM: Artificial Sequence
<220> FEATURE:
<223> OTHER INFORMATION: primer CR1-rev

<400> SEQUENCE: 2
taaacagagc ctccctatcc                                                     20

<210> SEQ ID NO 3
<211> LENGTH: 18
<212> TYPE: DNA
<213> ORGANISM: Artificial Sequence
<220> FEATURE:
<223> OTHER INFORMATION: primer CR1-gfwd

<400> SEQUENCE: 3
cctgtcatct ctgggagt                                                       18

<210> SEQ ID NO 4
<211> LENGTH: 20
<212> TYPE: DNA
<213> ORGANISM: Artificial Sequence
<220> FEATURE:
<223> OTHER INFORMATION: primer CR1-g2fwd

<400> SEQUENCE: 4
cggtgttcta tatcgaggtc                                                     20

<210> SEQ ID NO 5
<211> LENGTH: 21
<212> TYPE: DNA
<213> ORGANISM: Artificial Sequence
<220> FEATURE:
<223> OTHER INFORMATION: primer CR1-grev

<400> SEQUENCE: 5
ggagacacag gagtaggaaa g                                                   21
```

```
<210> SEQ ID NO 6
<211> LENGTH: 21
<212> TYPE: DNA
<213> ORGANISM: Artificial Sequence
<220> FEATURE:
<223> OTHER INFORMATION: primer CR1-g2rev

<400> SEQUENCE: 6
ggagacacag gagtaggaaa g                                              21

<210> SEQ ID NO 7
<211> LENGTH: 21
<212> TYPE: DNA
<213> ORGANISM: Artificial Sequence
<220> FEATURE:
<223> OTHER INFORMATION: primer CR2-fwd

<400> SEQUENCE: 7
ttagccccta ccatagtgct g                                              21

<210> SEQ ID NO 8
<211> LENGTH: 23
<212> TYPE: DNA
<213> ORGANISM: Artificial Sequence
<220> FEATURE:
<223> OTHER INFORMATION: primer CR2-rev

<400> SEQUENCE: 8
ttagtctaac actttctgga agc                                            23

<210> SEQ ID NO 9
<211> LENGTH: 23
<212> TYPE: DNA
<213> ORGANISM: Artificial Sequence
<220> FEATURE:
<223> OTHER INFORMATION: primer CR3-fwd

<400> SEQUENCE: 9
ctgagattaa tagtgcgatt acg                                            23

<210> SEQ ID NO 10
<211> LENGTH: 23
<212> TYPE: DNA
<213> ORGANISM: Artificial Sequence
<220> FEATURE:
<223> OTHER INFORMATION: primer CR3-rev

<400> SEQUENCE: 10
gctggatatt cgtataacat gtc                                            23

<210> SEQ ID NO 11
<211> LENGTH: 15
<212> TYPE: DNA
<213> ORGANISM: Artificial Sequence
<220> FEATURE:
<223> OTHER INFORMATION: primer (GTG)5

<400> SEQUENCE: 11
gtggtggtgg tggtg                                                     15

<210> SEQ ID NO 12
<211> LENGTH: 32
<212> TYPE: DNA
<213> ORGANISM: Artificial Sequence
<220> FEATURE:
<223> OTHER INFORMATION: primer 100-ECas7PstIF
```

<400> SEQUENCE: 12
agcagcctgc aggcaagagg aaatcgtcag tg                                      32

<210> SEQ ID NO 13
<211> LENGTH: 30
<212> TYPE: DNA
<213> ORGANISM: Artificial Sequence
<220> FEATURE:
<223> OTHER INFORMATION: primer 100-ECas7NcoIR

<400> SEQUENCE: 13
agcagcccat ggtcaatcct tactttctaa                                         30

<210> SEQ ID NO 14
<211> LENGTH: 32
<212> TYPE: DNA
<213> ORGANISM: Artificial Sequence
<220> FEATURE:
<223> OTHER INFORMATION: primer 100-ECas9XbaIF

<400> SEQUENCE: 14
agcagctcta gagtcgttag agggaggatt ac                                      32

<210> SEQ ID NO 15
<211> LENGTH: 31
<212> TYPE: DNA
<213> ORGANISM: Artificial Sequence
<220> FEATURE:
<223> OTHER INFORMATION: primer 100-ECas9PstIR

<400> SEQUENCE: 15
agcagcctgc agttaaaaat ctagcttagg c                                       31

<210> SEQ ID NO 16
<211> LENGTH: 21
<212> TYPE: DNA
<213> ORGANISM: Artificial Sequence
<220> FEATURE:
<223> OTHER INFORMATION: primer pNZ44fwd

<400> SEQUENCE: 16
ctaatgtcac taacctgccc c                                                  21

<210> SEQ ID NO 17
<211> LENGTH: 18
<212> TYPE: DNA
<213> ORGANISM: Artificial Sequence
<220> FEATURE:
<223> OTHER INFORMATION: primer pNZ44rev

<400> SEQUENCE: 17
gctttatcaa ctgctgct                                                      18

<210> SEQ ID NO 18
<211> LENGTH: 20
<212> TYPE: DNA
<213> ORGANISM: Artificial Sequence
<220> FEATURE:
<223> OTHER INFORMATION: primer CR4-fwd

<400> SEQUENCE: 18
gattcagttc ctcatagagc                                                    20

<210> SEQ ID NO 19
<211> LENGTH: 19

-continued

```
<212> TYPE: DNA
<213> ORGANISM: Artificial Sequence
<220> FEATURE:
<223> OTHER INFORMATION: primer CR4-rev

<400> SEQUENCE: 19
gacctcaacc aatcgattg                                          19

<210> SEQ ID NO 20
<211> LENGTH: 33
<212> TYPE: DNA
<213> ORGANISM: Artificial Sequence
<220> FEATURE:
<223> OTHER INFORMATION: primer 100-FCas7XbaIF

<400> SEQUENCE: 20
agcagctcta gacagtgata ataagttggt ggt                          33

<210> SEQ ID NO 21
<211> LENGTH: 32
<212> TYPE: DNA
<213> ORGANISM: Artificial Sequence
<220> FEATURE:
<223> OTHER INFORMATION: primer 100-FCas7PstIR

<400> SEQUENCE: 21
agcagcctgc agctgtcctt gtcaatcctt ac                           32

<210> SEQ ID NO 22
<211> LENGTH: 30
<212> TYPE: DNA
<213> ORGANISM: Artificial Sequence
<220> FEATURE:
<223> OTHER INFORMATION: primer 100-FCsn2PstIF

<400> SEQUENCE: 22
agcagcctgc aggccaattc agaggaaagg                              30

<210> SEQ ID NO 23
<211> LENGTH: 30
<212> TYPE: DNA
<213> ORGANISM: Artificial Sequence
<220> FEATURE:
<223> OTHER INFORMATION: primer 100-FCsn2NcoIR

<400> SEQUENCE: 23
agcagcccat ggcaagatgt gactgtcacc                              30

<210> SEQ ID NO 24
<211> LENGTH: 30
<212> TYPE: DNA
<213> ORGANISM: Artificial Sequence
<220> FEATURE:
<223> OTHER INFORMATION: primer 100-FCsn2XbaIFSW

<400> SEQUENCE: 24
agcagctcta gagccaattc agaggaaagg                              30

<210> SEQ ID NO 25
<211> LENGTH: 30
<212> TYPE: DNA
<213> ORGANISM: Artificial Sequence
<220> FEATURE:
<223> OTHER INFORMATION: primer 100-FCsn2PstIRSW

<400> SEQUENCE: 25
```
agcagcctgc agcaagatgt gactgtcacc                                              30

<210> SEQ ID NO 26
<211> LENGTH: 33
<212> TYPE: DNA
<213> ORGANISM: Artificial Sequence
<220> FEATURE:
<223> OTHER INFORMATION: primer 100-FCas7PstIFSW

<400> SEQUENCE: 26
agcagcctgc agcagtgata taagttggt ggt                                           33

<210> SEQ ID NO 27
<211> LENGTH: 32
<212> TYPE: DNA
<213> ORGANISM: Artificial Sequence
<220> FEATURE:
<223> OTHER INFORMATION: primer 100-FCas7NcoIRSW

<400> SEQUENCE: 27
agcagcccat ggctgtcctt gtcaatcctt ac                                           32

<210> SEQ ID NO 28
<211> LENGTH: 31
<212> TYPE: DNA
<213> ORGANISM: Artificial Sequence
<220> FEATURE:
<223> OTHER INFORMATION: primer 100-FCas9XbaIF

<400> SEQUENCE: 28
agcagctcta gagttgcgaa ttttcagata c                                            31

<210> SEQ ID NO 29
<211> LENGTH: 30
<212> TYPE: DNA
<213> ORGANISM: Artificial Sequence
<220> FEATURE:
<223> OTHER INFORMATION: primer 100-FCas9PstIR

<400> SEQUENCE: 29
agcagcctgc aggtaactgt gtaaggcgcc                                              30

<210> SEQ ID NO 30
<211> LENGTH: 36
<212> TYPE: DNA
<213> ORGANISM: Streptococcus thermophilus
<220> FEATURE:
<221> NAME/KEY: source
<222> LOCATION: (1)..(36)
<223> OTHER INFORMATION: /organism="Streptococcus thermophilus" /note=
      "strain 100-E & 100-F, CRISPR-1 Direct repeat" /mol_type=
      "unassigned DNA"

<400> SEQUENCE: 30
gtttttgtac tctcaagatt taagtaactg tacaac                                       36

<210> SEQ ID NO 31
<211> LENGTH: 36
<212> TYPE: DNA
<213> ORGANISM: Streptococcus thermophilus
<220> FEATURE:
<221> NAME/KEY: source
<222> LOCATION: (1)..(36)
<223> OTHER INFORMATION: /organism="Streptococcus thermophilus" /note=
      "strain 100-E & 100-F, CRISPR-1 Terminal repeat" /mol_type=
      "unassigned DNA"

<400> SEQUENCE: 31
gtttttgtac tctcaagatt taagtaactg tacagt 36

<210> SEQ ID NO 32
<211> LENGTH: 36
<212> TYPE: DNA
<213> ORGANISM: Streptococcus thermophilus
<220> FEATURE:
<221> NAME/KEY: source
<222> LOCATION: (1)..(36)
<223> OTHER INFORMATION: /organism="Streptococcus thermophilus" /note=
      "strain 100-E & 100-F, CRISPR-2 Direct repeat" /mol_type=
      "unassigned DNA"

<400> SEQUENCE: 32
gatataaacc taattacctc gagaggggac ggaaac 36

<210> SEQ ID NO 33
<211> LENGTH: 35
<212> TYPE: DNA
<213> ORGANISM: Streptococcus thermophilus
<220> FEATURE:
<221> NAME/KEY: source
<222> LOCATION: (1)..(35)
<223> OTHER INFORMATION: /organism="Streptococcus thermophilus" /note=
      "strain 100-E & 100-F, CRISPR-2 Terminal repeat" /mol_type=
      "unassigned DNA"

<400> SEQUENCE: 33
gatataaacc taattacctc gagaggggac ttttt 35

<210> SEQ ID NO 34
<211> LENGTH: 36
<212> TYPE: DNA
<213> ORGANISM: Streptococcus thermophilus
<220> FEATURE:
<221> NAME/KEY: source
<222> LOCATION: (1)..(36)
<223> OTHER INFORMATION: /organism="Streptococcus thermophilus" /note=
      "strain 100-E & 100-F, CRISPR-3 Direct repeat" /mol_type=
      "unassigned DNA"

<400> SEQUENCE: 34
gttttagagc tgtgttgttt cgaatggttc caaaac 36

<210> SEQ ID NO 35
<211> LENGTH: 28
<212> TYPE: DNA
<213> ORGANISM: Streptococcus thermophilus
<220> FEATURE:
<221> NAME/KEY: source
<222> LOCATION: (1)..(28)
<223> OTHER INFORMATION: /organism="Streptococcus thermophilus" /note=
      "strain 100-F, CRISPR-4 Direct repeat" /mol_type="unassigned DNA"

<400> SEQUENCE: 35
gtttttcccg cacacgcggg ggtgatcc 28

<210> SEQ ID NO 36
<211> LENGTH: 28
<212> TYPE: DNA
<213> ORGANISM: Streptococcus thermophilus
<220> FEATURE:
<221> NAME/KEY: source
<222> LOCATION: (1)..(28)
<223> OTHER INFORMATION: /organism="Streptococcus thermophilus" /note=
      "strain 100-F, CRISPR-4 Terminal repeat" /mol_type="unassigned
      DNA"

-continued

```
<400> SEQUENCE: 36
gtttttcccg cacacgcggg ggtgattc                                          28
```